(12) United States Patent
Ahlberg et al.

(10) Patent No.: US 8,801,741 B2
(45) Date of Patent: Aug. 12, 2014

(54) FLAT BLADE SHIELDED OBTURATOR

(75) Inventors: Russell E. Ahlberg, Rancho Santa Margarita, CA (US); Martin Ponisio, Aliso Viejo, CA (US); Luca Pesce, Lake Forest, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1872 days.

(21) Appl. No.: 11/744,108

(22) Filed: May 3, 2007

(65) Prior Publication Data

US 2007/0260275 A1 Nov. 8, 2007

Related U.S. Application Data

(60) Provisional application No. 60/746,313, filed on May 3, 2006, provisional application No. 60/912,679, filed on Apr. 18, 2007, provisional application No. 60/915,545, filed on May 2, 2007.

(51) Int. Cl.
*A61B 17/34* (2006.01)

(52) U.S. Cl.
USPC ........................................................ 606/185

(58) Field of Classification Search
USPC ............. 606/167, 184, 185, 170; 604/165.01, 604/164.01–170.03, 264
See application file for complete search history.

(56) References Cited

U.S. PATENT DOCUMENTS

| 4,601,710 A | 7/1986 | Moll |
| 4,654,030 A | 3/1987 | Moll et al. |
| 4,931,042 A | 6/1990 | Holmes et al. |
| 5,030,206 A | 7/1991 | Lander |
| 5,114,407 A | 5/1992 | Burbank |
| 5,224,952 A | 7/1993 | Deniega et al. |
| 5,226,426 A | 7/1993 | Yoon |
| 5,246,425 A | 9/1993 | Hunsberger et al. |
| 5,275,583 A | 1/1994 | Crainich |
| 5,290,243 A | 3/1994 | Chodorow et al. |
| 5,312,354 A | 5/1994 | Allen et al. |
| 5,314,417 A | 5/1994 | Stephens et al. |
| 5,318,580 A | 6/1994 | Gresl, Jr. |
| 5,330,432 A | 7/1994 | Yoon |
| 5,338,305 A | 8/1994 | Plyley et al. |
| 5,342,382 A | 8/1994 | Brinkerhoff et al. |
| 5,350,393 A | 9/1994 | Yoon |
| 5,360,405 A | 11/1994 | Yoon |

(Continued)

FOREIGN PATENT DOCUMENTS

WO   WO 94/09712   5/1994

OTHER PUBLICATIONS

The International Bureau of WIPO, The International Preliminary Report on Patentability for International Patent Applicationi No. PCT/US07/68164 mailed Nov. 13, 2008.

(Continued)

*Primary Examiner* — Thomas McEvoy

(74) *Attorney, Agent, or Firm* — John F. Heal; Patrick Y. Ikehara

(57) ABSTRACT

A shielded bladed obturator is provided with a shield lockout that prevents retraction of a shield to expose a blade for cutting. The shield lockout in one aspect has a rotational switch interacting with a longitudinal extending shield to lock and unlock the shield. A blade exposure and coverage system is also provided.

18 Claims, 44 Drawing Sheets

(56) References Cited

U.S. PATENT DOCUMENTS

| | | |
|---|---|---|
| 5,364,365 A | 11/1994 | Wortrich |
| 5,364,372 A | 11/1994 | Danks et al. |
| 5,366,445 A | 11/1994 | Haber et al. |
| 5,372,588 A | 12/1994 | Farley et al. |
| 5,387,197 A | 2/1995 | Smith et al. |
| 5,399,167 A | 3/1995 | Deniega |
| 5,411,515 A | 5/1995 | Haber et al. |
| 5,417,705 A | 5/1995 | Haber et al. |
| 5,462,532 A | 10/1995 | Gresl |
| 5,486,190 A | 1/1996 | Green |
| 5,527,335 A | 6/1996 | Bolduc et al. |
| 5,536,256 A | 7/1996 | Yoon |
| 5,538,509 A | 7/1996 | Dunlap et al. |
| 5,569,289 A | 10/1996 | Yoon |
| 5,584,848 A | 12/1996 | Yoon |
| 5,599,347 A * | 2/1997 | Hart et al. ............... 606/42 |
| 5,609,604 A | 3/1997 | Schwemberger et al. |
| 5,618,297 A | 4/1997 | Hart et al. |
| 5,620,456 A | 4/1997 | Sauer et al. |
| 5,624,459 A | 4/1997 | Kortenbach et al. |
| 5,634,934 A | 6/1997 | Yoon |
| 5,645,076 A | 7/1997 | Yoon |
| 5,645,556 A | 7/1997 | Yoon |
| 5,645,557 A | 7/1997 | Yoon |
| 5,665,072 A | 9/1997 | Yoon |
| 5,665,102 A | 9/1997 | Yoon |
| 5,674,237 A | 10/1997 | Ott |
| 5,676,156 A | 10/1997 | Yoon |
| 5,676,681 A | 10/1997 | Yoon |
| 5,690,663 A | 11/1997 | Stephens |
| 5,697,947 A | 12/1997 | Wolf et al. |
| 5,776,112 A | 7/1998 | Stephens et al. |
| 5,779,680 A | 7/1998 | Yoon |
| 5,807,402 A | 9/1998 | Yoon |
| 5,851,216 A | 12/1998 | Allen |
| 5,868,773 A | 2/1999 | Danks et al. |
| 5,904,699 A | 5/1999 | Schwemberger et al. |
| 5,916,232 A | 6/1999 | Hart |
| 5,980,493 A | 11/1999 | Smith et al. |
| 5,984,941 A | 11/1999 | Wilson et al. |
| 5,997,510 A | 12/1999 | Schwemberger |
| 6,017,356 A | 1/2000 | Frederick et al. |
| 6,063,099 A | 5/2000 | Danks et al. |
| 6,099,544 A | 8/2000 | Wolf et al. |
| 6,238,407 B1 | 5/2001 | Wolf et al. |
| 6,319,266 B1 | 11/2001 | Stellon et al. |
| 6,340,358 B1 | 1/2002 | Bohannon et al. |
| 6,402,770 B1 | 6/2002 | Jessen |
| 6,450,992 B1 | 9/2002 | Cassidy |
| 6,716,201 B2 | 4/2004 | Blanco |
| 6,837,874 B1 | 1/2005 | Popov |
| 6,939,351 B2 | 9/2005 | Eckman |
| 6,960,164 B2 | 11/2005 | O'Heeron |
| 2001/0029387 A1 | 10/2001 | Wolf et al. |
| 2002/0026207 A1 | 2/2002 | Stellon et al. |
| 2002/0161387 A1 | 10/2002 | Blanco |
| 2003/0060770 A1 | 3/2003 | Wing et al. |
| 2004/0049173 A1 | 3/2004 | White et al. |
| 2004/0116864 A1 | 6/2004 | Boudreaux |
| 2004/0147949 A1 | 7/2004 | Stellon et al. |
| 2004/0230155 A1 | 11/2004 | Blanco et al. |
| 2005/0070947 A1 | 3/2005 | Franer et al. |
| 2005/0209623 A1 | 9/2005 | Patton |
| 2006/0030870 A1 | 2/2006 | Staudner |
| 2006/0052811 A1 | 3/2006 | Blanco |

OTHER PUBLICATIONS

The International Searching Authority/US, The International Search Report and the Written Opinion of the International Searching Authority for International Patent No. PCT/US/07/68164 mailed Aug. 7, 2008.

European Patent Office, Supplementary European Search Report for European Application No. EP 07761842, entitled "Flat Blade Shielded Obturator" dated Feb. 7, 2013.

\* cited by examiner

FLAT BLADE SHIELDED OBTURATOR

CROSS-REFERENCE TO RELATED APPLICATIONS

This application claims the benefit of U.S. Provisional Application No. 60/746,313, filed May 3, 2006; U.S. Provisional Application No. 60/912,679, filed Apr. 18, 2007; and U.S. Provisional Application No. 60/915,545, filed May 2, 2007, the disclosures of which are hereby incorporated by reference as if set forth in full herein.

BACKGROUND

This invention relates generally to trocars or access ports used in endoscopic or laparoscopic surgeries and more particularly, to flat blade shielded obturators.

A surgical access port or trocar generally has a cannula and a valve housing coupled to one end of the cannula and an obturator inserted into the cannula has a shaft with a sharp blade or tip at one end of the shaft. In operation, the trocar cannula extends across a body wall, e.g., the abdominal wall, providing access into a body cavity, such as the abdominal cavity. The obturator facilitates the placement of the trocar by puncturing and/or penetrating the tissue forming the body wall.

In one example, the obturator is inserted through the cannula and its sharp bladed tip extends beyond one end of the cannula. The sharp bladed tip of the obturator cuts tissue as the trocar and obturator are moved through the body wall. Once the trocar and obturator are operatively positioned, the obturator can be removed from the trocar body leaving the cannula to provide working-channel access into the body cavity.

With the body wall penetrated, the sharp bladed tip can be covered or protected. For example, a spring-loaded tubular safety shield which surrounds the shaft of the obturator may move forward to cover the tip of the obturator once resistance to the movement of the safety shield, e.g., from the body wall, is removed. As such, the cutting stops once the body wall has been penetrated. However, a relatively large force may be required to cause the tip of an obturator to penetrate the body wall. Once the tip penetrates the body wall, resistance to penetration is removed and the tip of the obturator is suddenly free to reach into the body cavity and cause additional cutting. Failure to stop this cutting action can result in complications. Obturators having spring-loaded tubular safety shields may require larger incisions and may require considerable time to move the shield to cover the tip, the shield possessing a relatively large mass.

SUMMARY

Generally, a flat blade shielded obturator is provided. In one aspect, an obturator comprises a handle and a shaft. The handle has a rotatable switch arranged to rotate about a rotational axis from a first position to a second position. The shaft is connected to the handle and has a longitudinal axis parallel with the rotational axis. The shaft has a movable portion and a fixed portion with a blade connected to the fixed portion of the shaft. The rotatable switch in the first position obstructs the movable portion of the shaft to prevent movement of the movable portion of the shaft along the longitudinal axis and in the second position frees the movable portion of the shaft to allow movement of the movable portion of the shaft along the longitudinal axis.

In one aspect, an obturator comprises a handle and a shaft. The handle has a manually engagable switch arranged to rotate about a rotational axis from a first position to a second position. The shaft is connected to the handle and has a longitudinal axis parallel with the rotational axis. The shaft has a movable portion and a fixed portion with a blade connected to the fixed portion of the shaft. The switch has means for aligning with the movable portion of the shaft to prevent movement of the movable portion of the shaft along the longitudinal axis and having means for misaligning with the shaft to allow movement of the movable portion of the shaft.

In one aspect, an obuturator comprises a handle and a shaft. The handle has a manually engagable switch arranged to rotate about a rotational axis from a first position to a second position. The shaft is connected to the handle and has a longitudinal axis parallel with the rotational axis, the shaft having a movable shield and a fixed shield with a blade connected to the fixed shield. The switch has a planar surface and a slot. The planar surface of the switch being aligned with the shaft prevents movement of the movable shield along the longitudinal axis. The slot of the switch being aligned with the shaft allows movement of the movable shield.

Many of the attendant features of the present invention will be more readily appreciated as the same becomes better understood by reference to the foregoing and following description and considered in connection with the accompanying drawings in which like reference symbols designate like parts throughout.

DETAILED DESCRIPTION

In one aspect, an obturator is provided having a handle and a shaft. The handle is on a proximal end of the shaft and a sharp bladed tip coupled on the other (distal) end of the shaft. The distal end of an obturator is configured to minimize the insertion force. The obturator is also configured to provide control that is maintained during entry. The obturator also has a shield that protects the blade before use and covers the blade as it is passes through the abdominal wall. In one aspect, the shield is a single monolithic piece shielding the blade or at least one section or components situated to protect or cover the blade.

Other relatively heavy blade and supporting mechanism add significantly to the actuation time required for retraction. This actuation time leaves the blade exposed, potentially allowing undesired cutting to continue. This configuration can also fail to provide an incision which accommodates the full diameter of the obturator. As a result, insertion forces required to penetrate the body wall tend to be relatively high.

Figure 1:
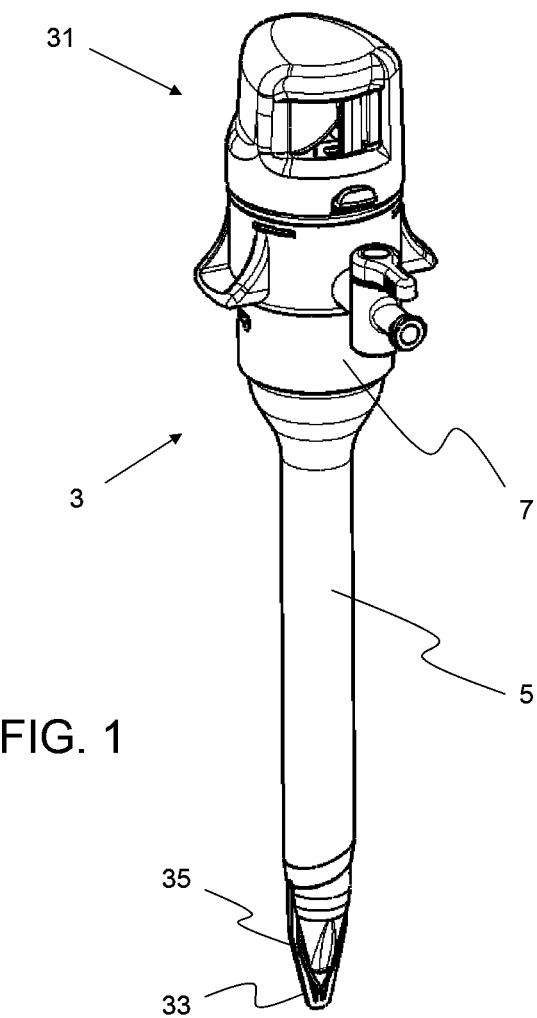
FIG. 1 is a perspective view of a trocar system with a shielded bladed obturator in accordance with various aspects of the present invention.

In FIG. 1, a trocar with an obturator 3 inserted into a cannula 5 is shown. The obturator 3 has a handle 31, shield 33 and a blade 35. A housing 7 is attached to the proximal end of the cannula 51. The trocar cannula 5 provides surgical instrument access into the body cavity with the obturator 3 removed. The trocar housing 7 releasbly attached to the trocar cannula 51 contains one or more trocar seals to maintain pneumoperitoneum when the obturator and/or surgical instruments are inserted through and withdrawn from the trocar 5.

Figure 2:
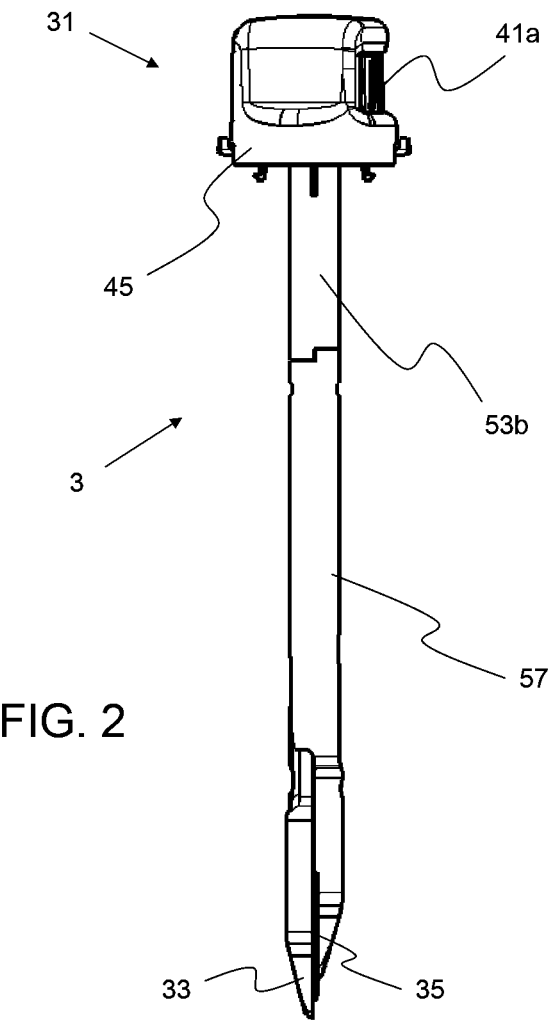
FIG. 2 is a side view of a shielded bladed obturator in accordance with various aspects of the present invention.
Figure 3:
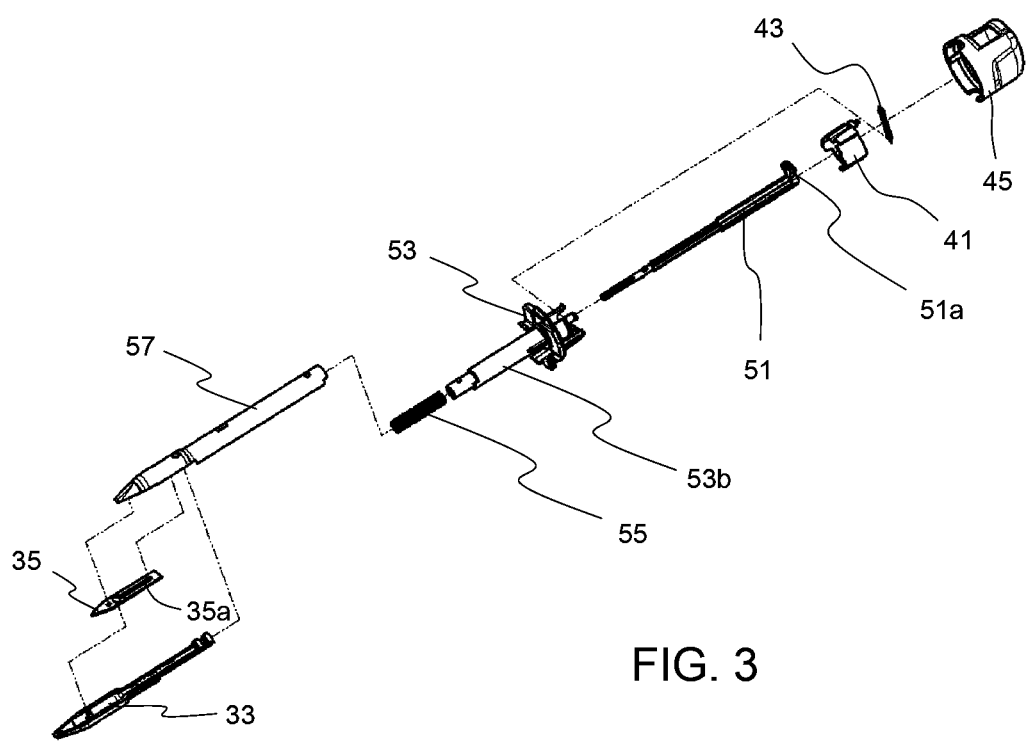
FIG. 3 is an exploded view of a shielded bladed obturator in accordance with various aspects of the present invention.

Referring now also to FIGS. 2-3, the obturator handle 31 includes a cover 45 with a switch 41. The switch 41 is generally circular and arranged to rotate around the longitudinal axis of the obturator 3. The switch has a lever 41a. The lever protrudes through an opening of the periphery of the cover 45 allowing the lever 41a to be accessible by a user, e.g., a surgeon. A spring 43, such as an extension, leaf or the like, is attached on one end to the switch 41, e.g., post 41b. The other end of the spring is attached to a projection 53a extending from a base plate 53. The switch 41 and cover 45 are mounted on the base plate 53, securing the switch 41 between the cover 45 and base plate 53. Extending away from the base plate and cover along the longitudinal axis of the obturator is an outer shaft 53b. The outer shaft 53b is tubular having a lumen through which an inner shaft 51 extends there through. A projection or flange 51a extends from the proximal end of the inner shaft orthogonally from the longitudinal axis of the inner shaft 51. The flange 51a prevents the inner shaft 51 from completely extending through the lumen of the outer shaft 53b. The inner shaft 51 slides relative to the outer shaft 53b and is attached to a blade shield 33. The blade shield is also moveable, e.g., sliding as the shaft 51 slides. In one aspect, the inner shaft 51 and the blade shield 33 are integral and/or monolithically formed.

A compression spring 55 surrounds a portion of the inner shaft 51 and biases the inner shaft 51 and blade shield 33 distally. Both the compression spring 55 and a portion of the inner shaft 51 are housed within a fixed shield 57 that is generally tubular. One end of the fixed shield 57 is connected to the outer shaft 53b and the other end has one or more projections that extend through a slot in the blade 35 securing the blade 35 to the fixed shield 57. A projection or hook extends from the blade shield and through the slot 35a in the blade 35. In one aspect, the hook is situated and slidable between two projections extending from the fixed shield 57 along the slot 35a of the blade 35. The other end of the blade shield 33 is connected to the inner shaft 51. The blade shield 33 and the inner shaft 51 have corresponding projections and slots to secure the inner shaft to the blade shield 33. As such, as the blade shield 33 moves, the inner shaft 51 also moves and vice versa. The blade shield 33 abuts one end of the compression spring 55. The other end of the compression spring 55 abuts the outer shaft 53b. The compression spring 55 biases the blade shield 33 forward covering one side of the blade 35. An example of an asymmetrical blade shield configuration is described in U.S. Pat. No. 5,916,232, the disclosure of which is incorporated by reference as if set forth in full herein. A sharp bladed tip of an obturator can comprise of a blade having a symmetrical triangular form. This blade configuration can tend to form an opening, which results in a wound having three cuts each radiating from a central puncture or penetration point. Single blade obturators penetrate the body wall through a single incision.

In one aspect, a lever is coupled to the handle of the obturator that is manually actuated to unlock the shield (which protects the cutting blade when not in use). An extension spring is used that is connected between the rotating lever switch and the fixed shaft. The spring holds the lever biased to one side. As the lever is rotated, the spring is pulled over the centerline of the obturator and pulls the lever to the other side. At this location, the shield is unlocked. When the obturator is pushed through the abdominal wall, the cam shaft of the shield slides up and the blades become exposed for cutting. At the same time, the other end of the cam shaft pushes on a cam surface which is part of the lever switch causing the switch to rotate back towards its original position. As the lever switch is being rotated by the cam shaft, the extension spring is pulled back over the centerline, pulling it in the opposite direction. Once through the abdominal wall, the cam shaft resets itself over the blade, and the lever switch resets, locking the shield over the blade.

Referring also to FIGS. 4-9, the switch 41 that is coupled to the inner shaft 51 that is coupled to the blade shield 33 controls or regulates the arming/disarming or unlocking/locking of the blade shield 33, e.g., allowing the blade shield 33 to slidably retract back towards a proximal direction. Initially, the switch 41 is in the armed or locked position, such that the blade shield 33 is locked or prevented from retracting to expose the blade 35 for cutting.

Figure 4:
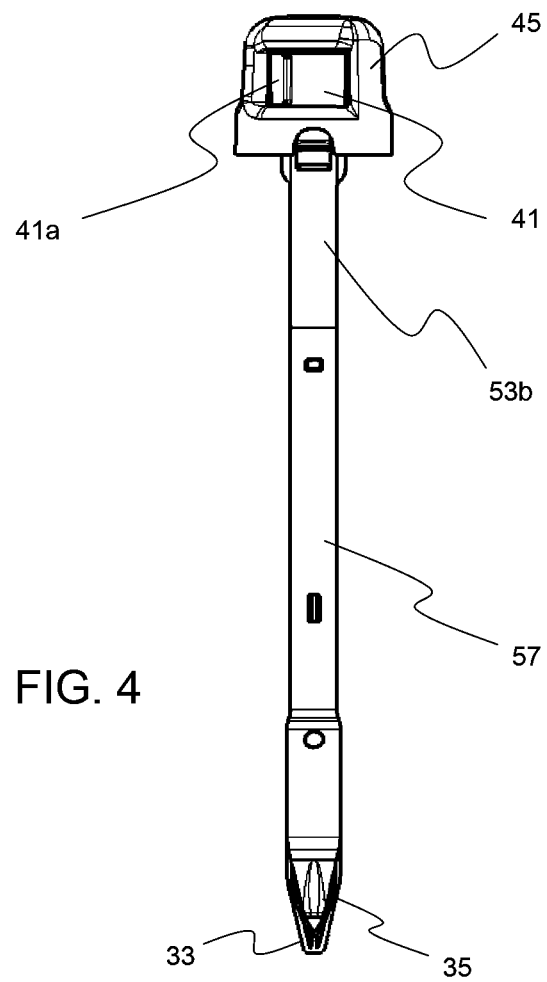
FIG. 4 is a side view of a shielded bladed obturator in accordance with various aspects of the present invention.
Figure 5:
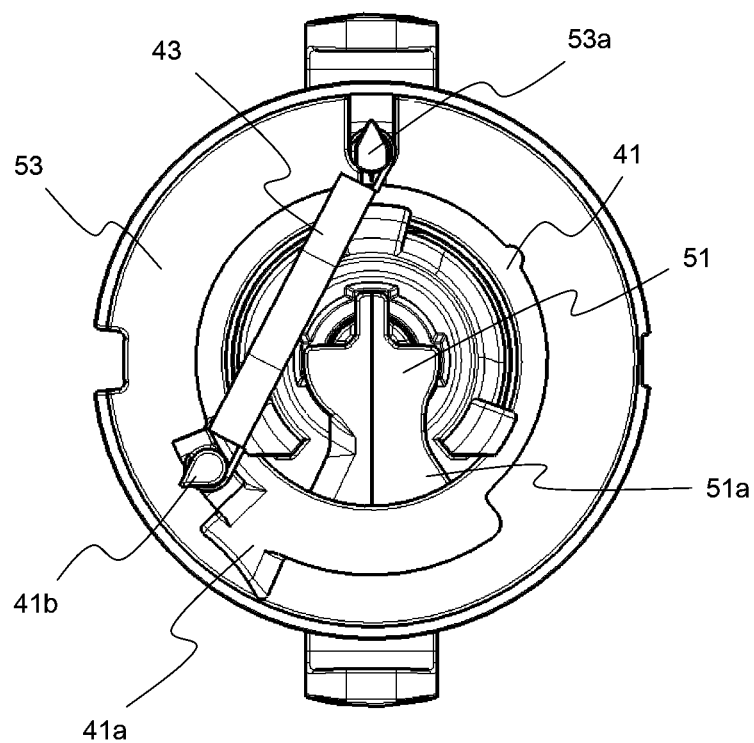
FIG. 5 is a top view of a shielded bladed obturator with a cover removed/hidden in accordance with various aspects of the present invention.
Figure 6:
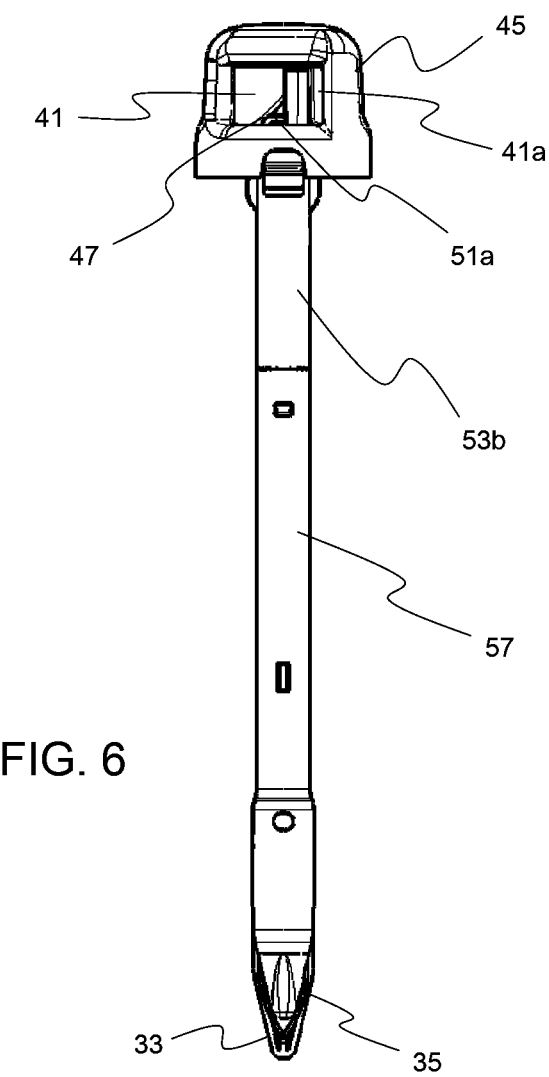
FIG. 6 is a side view of a shielded bladed obturator in accordance with various aspects of the present invention.
Figure 7:
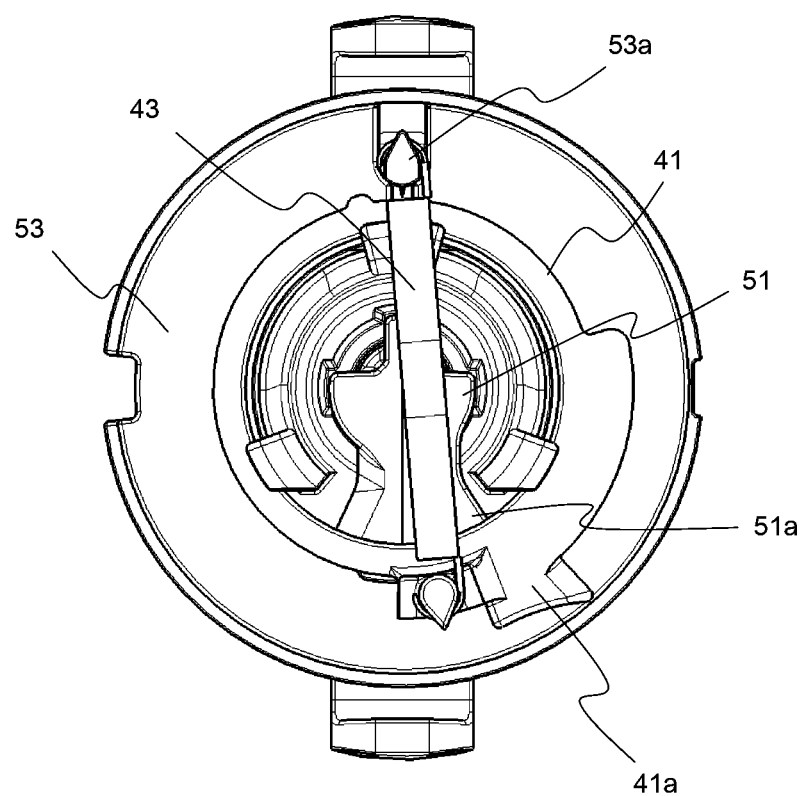
FIG. 7 is a top view of a shielded bladed obturator with a cover removed/hidden in accordance with various aspects of the present invention.
Figure 8:
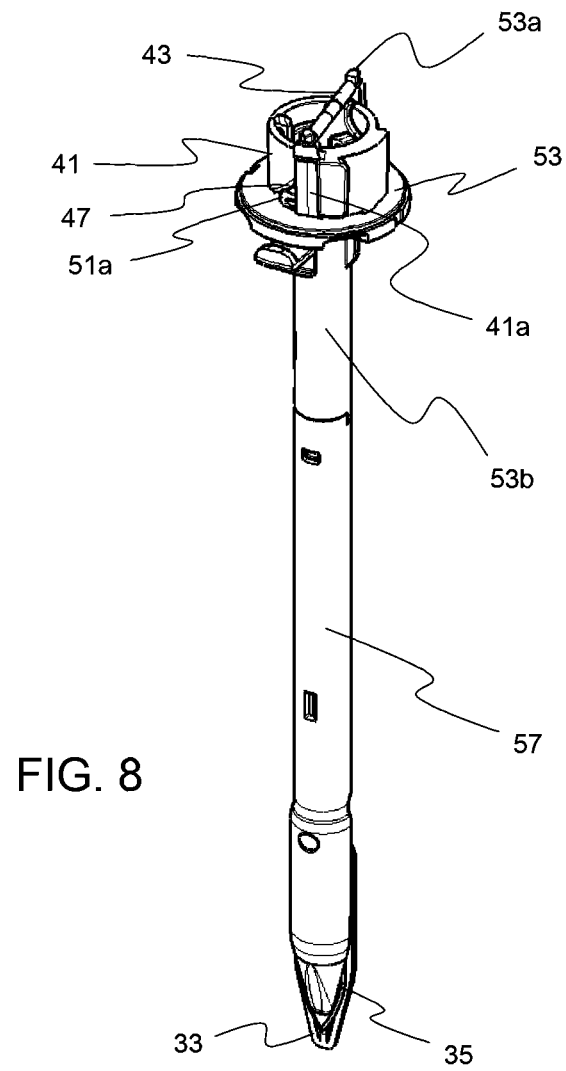
FIG. 8 is a perspective view of a shielded bladed obturator with a cover removed/hidden in accordance with various aspects of the present invention.
Figure 9:
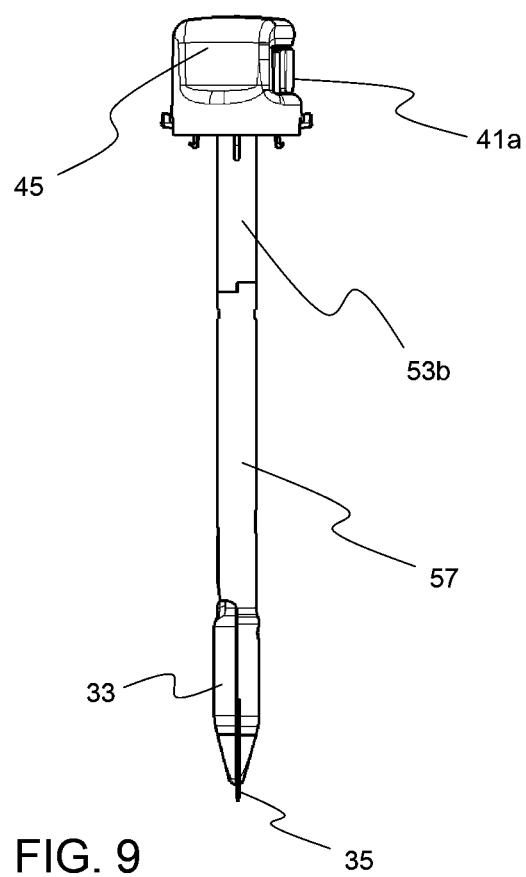
FIG. 9 is a side view of a shielded bladed obturator in accordance with various aspects of the present invention.

In FIGS. 4-5, the switch 41 in the armed position is situated to block movement of the inner shaft 51. In one aspect, an outer surface or edge of the switch 41 abuts or is in contact with a ledge or projection of the inner shaft 51 extending laterally from the longitudinal axis of the inner shaft. The interaction of the switch 41 with the inner shaft 51 controls the activation or deactivation of the blade shield 33. The cover 45 prevents further movement of the switch by limiting the longitudinal movement of the switch 41 and also adds stability to the switch 41. The extension spring 43 coupled to the switch 41 biases the switch towards the initial or armed position. The extension spring 43 generally extends to an over center condition at the initial or armed position of the switch 41, e.g., more towards one portion or half of the switch or base plate 53. As such, the extension spring 43 in the locked position tends to pull the switch 41 towards a clockwise direction.

Referring now to FIGS. 6-9, the switch 41 via the lever 41a is manually actuated to move or rotate from the armed position to the disarmed or unlocked position. For example, the switch 41 is rotated in a counter-clockwise direction. As the switch 41 is rotated toward the disarmed position, the extension spring 43 is moved from over center at the initial/locked position towards an over center position at the unlocked position, e.g., more towards an opposing portion or half of the switch 41 or base plate 53. As such, the extension spring 43 in the unlocked portion or position tends to pull the switch 41 towards a counter-clockwise direction. Such manual actuation overcomes the biasing force of the extension spring 43 that tends to drive the switch towards the armed position. As such, if the lever 41a is released prior to reaching the disarmed position, the switch 41 moves back to the armed position. In general, if the lever 41a is released prior to reaching the center point of the switch 41, i.e., where the extension spring 43 changes from biasing the switch 41 in one direction to an opposing direction, the switch 41 returns back to its starting position.

In the disarmed position, the ledge 51a of the inner shaft 51 abuts the slanted surface or slot 47 of the switch 41 thereby preventing further rotational movement of the switch 41 backed to the armed position. In one aspect, the switch 41, when in or moved into the disarmed position, engages a projection or slot on the base plate 53 to maintain the switch in the unlock position. In one aspect, when in the disarmed position, the lever 45 recedes within the cover or within a slot or cavity in the cover thereby hiding and preventing inadvertent or undesired activation of the lever to re-lock the blade shield.

With the switch 41 in the disarmed position, the inner shaft 51 and the blade shield 33 are allowed to retract largely unobstructed by the switch 41. In the disarmed position, the ledge 42 of switch 41 does not abut the ledge 51a extending from the inner shaft 51, such that the inner shaft is prevented from traveling longitudinally. Rotational movement of the switch to the disarmed position positions a cavity or a slanted cam slot 47 over the ledge 51a of the inner shaft 51. As such, the inner shaft 51 is provided a longitudinal path through the switch 41 and as pressure or force is applied to the blade shield 33, the blade shield can retract causing the inner shaft 51 to retract. The retracting blade shield 33 exposes blade 35 thereby allowing the surgeon to cut tissue with the blade 35. The compression spring 55 coupled to the blade shield 33 and inner shaft 51 resists the retraction movement and facilitates forward movement of the blade to enhance the speed to recover the exposed blade 35. Thus, if force or pressure is removed or reduced on the blade shield 33 sufficient to no longer overcome the force from the compression spring 55, the blade shield 33 moves forward.

As the inner shaft 51 and blade shield 33 retracts to expose the blade 35, the inner shaft 51 forces or moves the switch 41 towards the armed or locked position. With the ledge 51a of the inner shaft retracting or moving longitudinally along the slanted surface 47 in the cavity or notch in the switch 41, the switch 41 is forced to rotate towards the armed position, e.g., clockwise. As such, as the extension spring 43 moves over center, the extension spring 43 biases the switch 41 towards the armed or locked position. With force or pressure removed from the blade shield 33 and the inner shaft 51, the blade shield 33 and inner shaft 51 move forward. When the switch 41 is in the armed or locked position, the switch 41 with ledge 42 interacting with ledge 51a of the inner shaft 51 prevents retraction of the blade shield 33 until the lever 45 of the switch 41 is again manually actuated and moved to the disarmed position.

Figure 10:
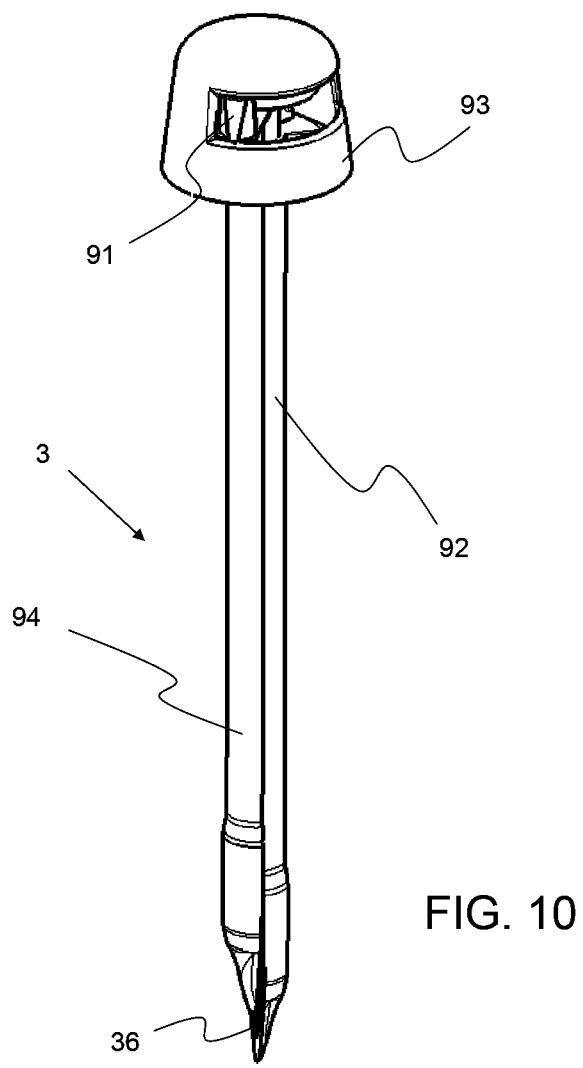
FIG. 10 is a perspective view of a shielded bladed obturator in accordance with various aspects of the present invention.
Figure 11:
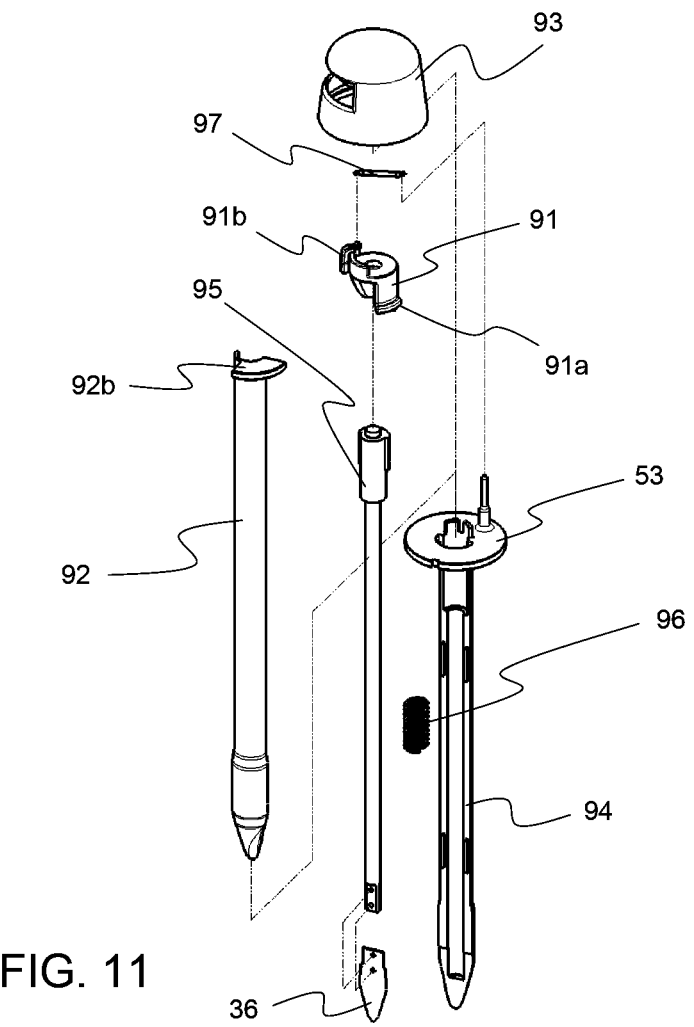
FIG. 11 is an exploded view of a shielded bladed obturator in accordance with various aspects of the present invention.
Figure 12:
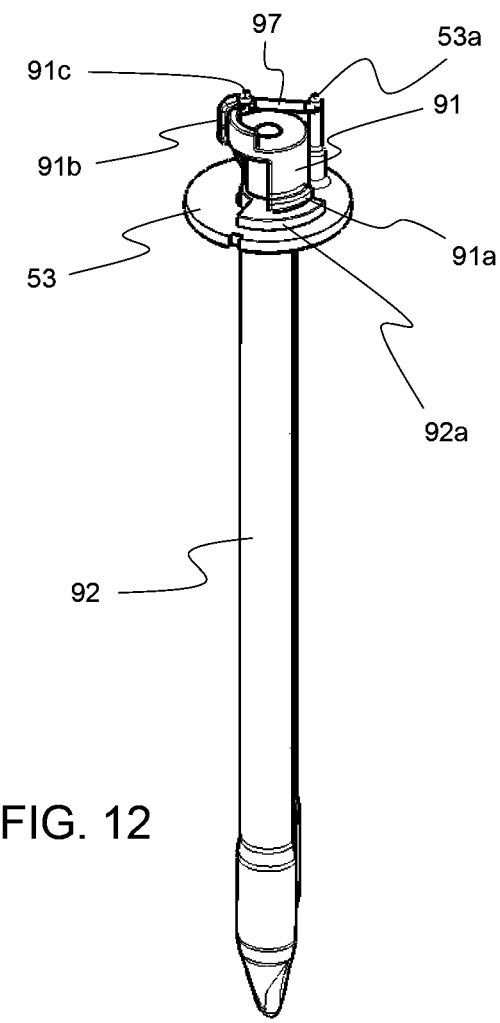
FIG. 12 is a perspective view of a shielded bladed obturator with a cover removed/hidden in accordance with various aspects of the present invention.

In FIGS. 10-12, the obturator 3 has a switch 91 that obstructs movement of a cam shaft 92 that acts as a blade shield preventing exposure of blade 35 for cutting. A cover 93 secures the switch 91 to the base plate 53 of the fixed shaft 94 of the obturator. An extension spring 97 connects the switch to the base plate 53 and biases the switch to the locked position obstructing retraction of the cam shaft 92. A middle pin 95 coupled with a compression spring 96 connects the switch 91 to the cam shaft 92 and biases the cam shaft to cover or prevent exposure of the blade 36 for cutting. A lever 51b extending from the switch 91 through a slot in the cover 93 allows manipulation of the switch 91. The switch in the locked or armed position has an edge or flange 91a interacting with an edge or flange 92a thereby obstructing and preventing retraction of the cam shaft 92.

Figure 13:
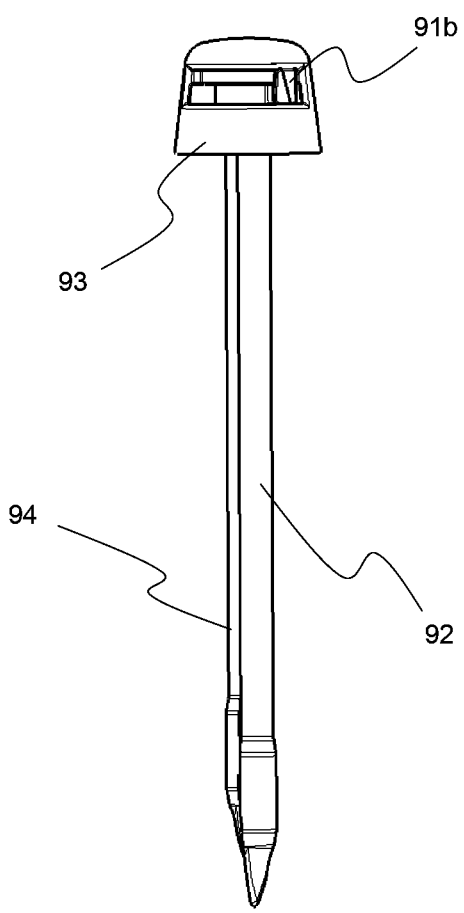
FIG. 13 is a side view of a shielded bladed obturator in accordance with various aspects of the present invention.
Figure 14:
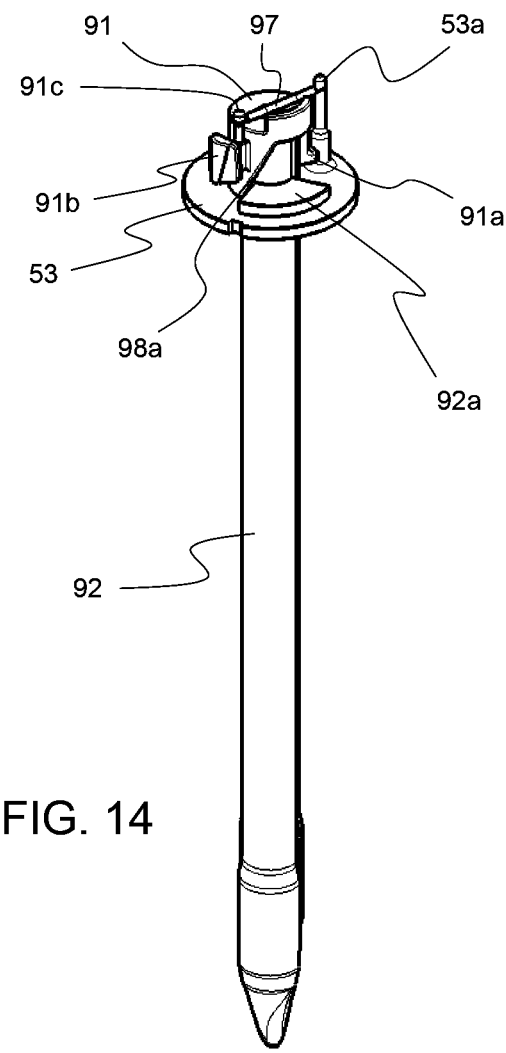
FIG. 14 is a perspective view of a shielded bladed obturator with a cover removed/hidden in accordance with various aspects of the present invention.
Figure 15:
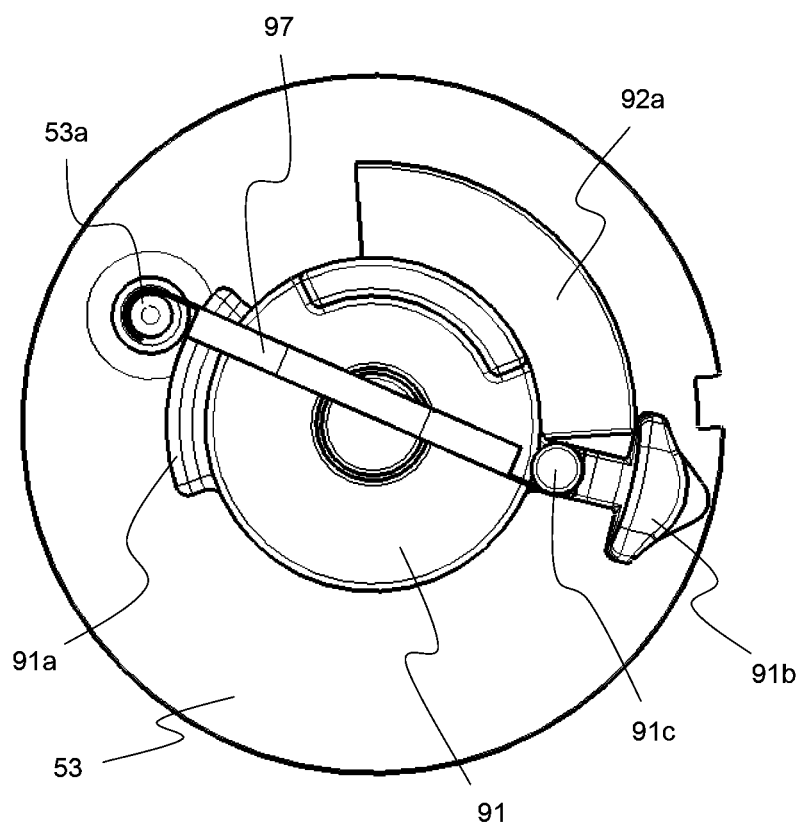
FIG. 15 is a top view of a shielded bladed obturator with a cover removed/hidden in accordance with various aspects of the present invention.

Referring now also to FIGS. 13-15, when the switch is moved to an unlocked position, the edge 91a of the switch 91 is rotated out of the path of the flange 92a of the cam shaft 92. A slot 98 in the switch is positioned in line with the flange 92a and a ramped cam surface 98a abuts the flange 92a of the cam shaft 92. With the switch in the unlocked position, the extension spring 97 biases the switch 91 towards the unlocked position. In particular, the extension spring 97 produces a force that generates a moment about the centroid of the switch 91, such that the moment forces the switch to rotate towards the unlocked position, e.g., counter-clockwise. The interaction with the ramped cam surface 98a abutting the flange 92a of the cam shaft 92 limits further rotation of the switch 91. In one aspect, the cam shaft 92 could comprises of multiple component having a distal portion or component for contacting tissue and a proximal portion or component interacting with the switch 91.

Figure 16:
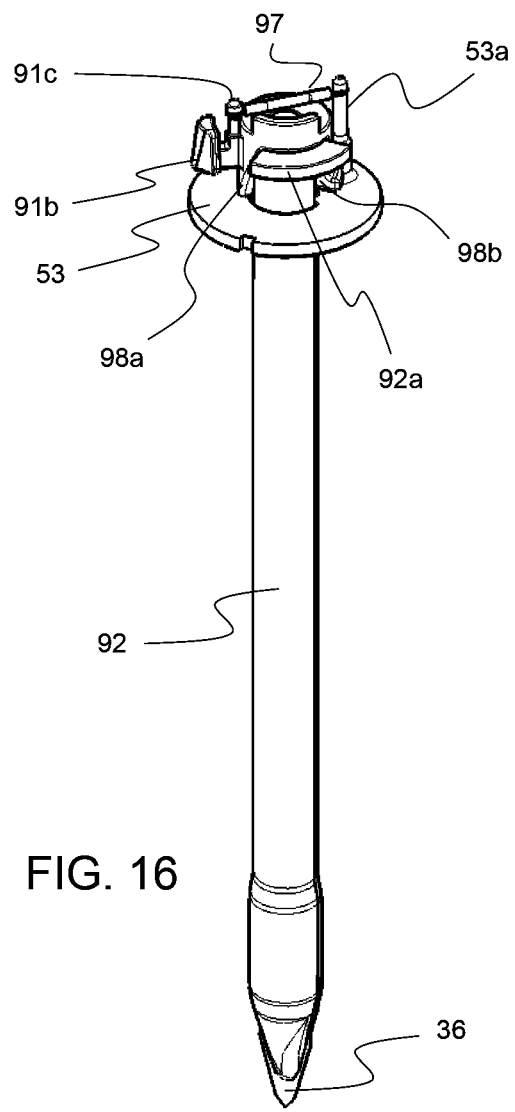
FIG. 16 is a perspective view of a shielded bladed obturator with a cover removed/hidden in accordance with various aspects of the present invention.
Figure 17:
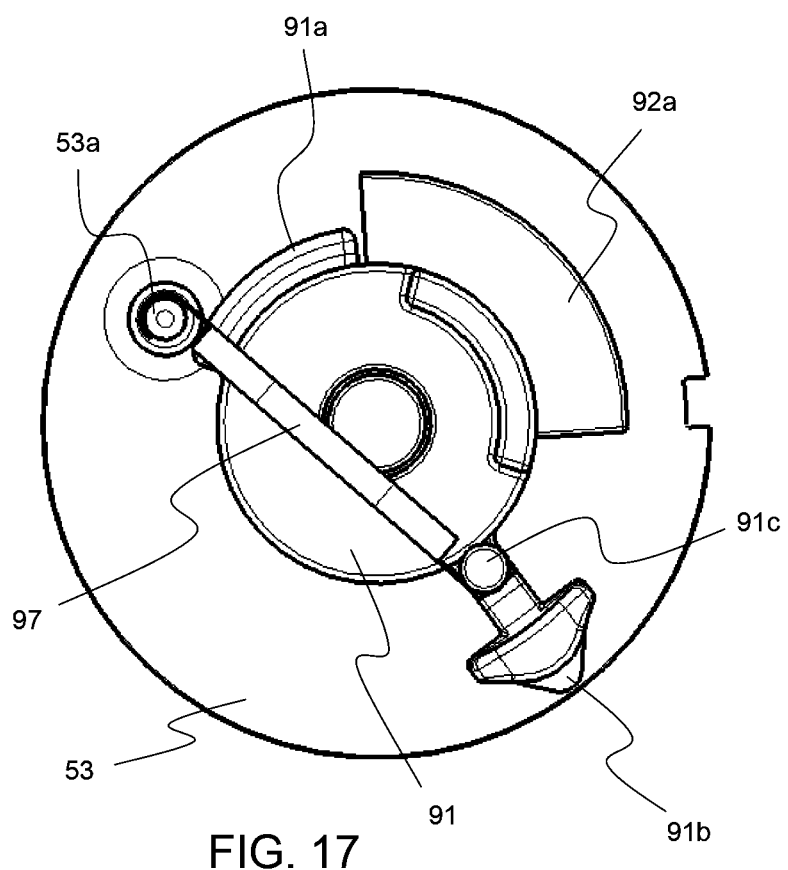
FIGS. 17-18 are top views of a shielded bladed obturator with a cover removed/hidden in accordance with various aspects of the present invention.
Figure 18:
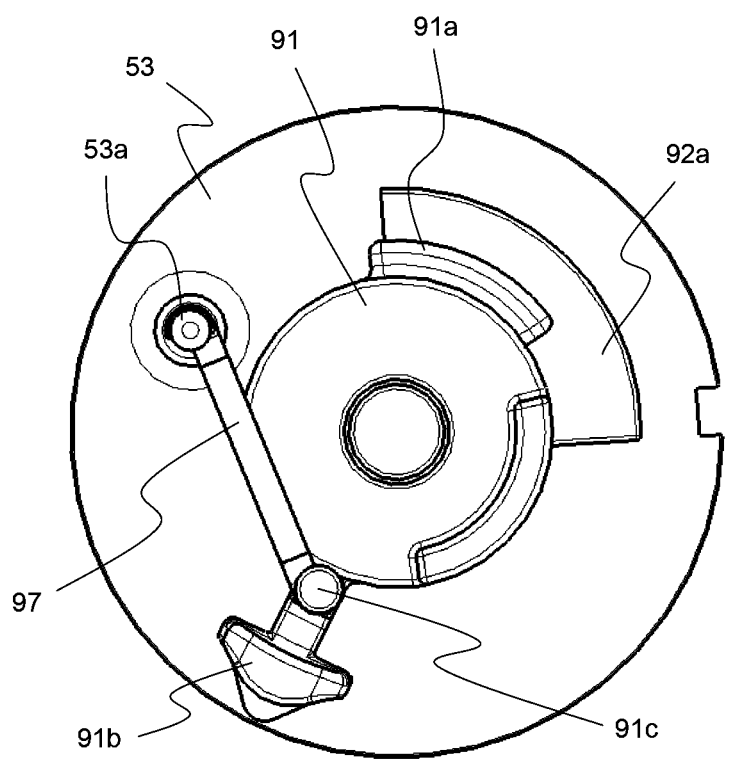
Figure 19:
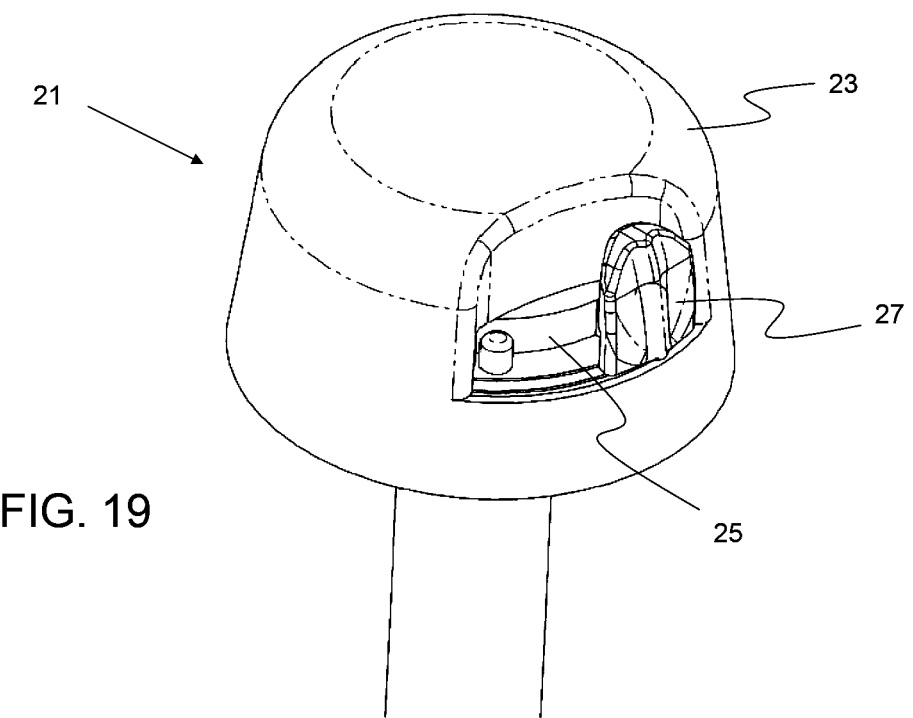
FIG. 19 is a perspective view of a shielded bladed obturator in accordance with various aspects of the present invention.
Figure 20:
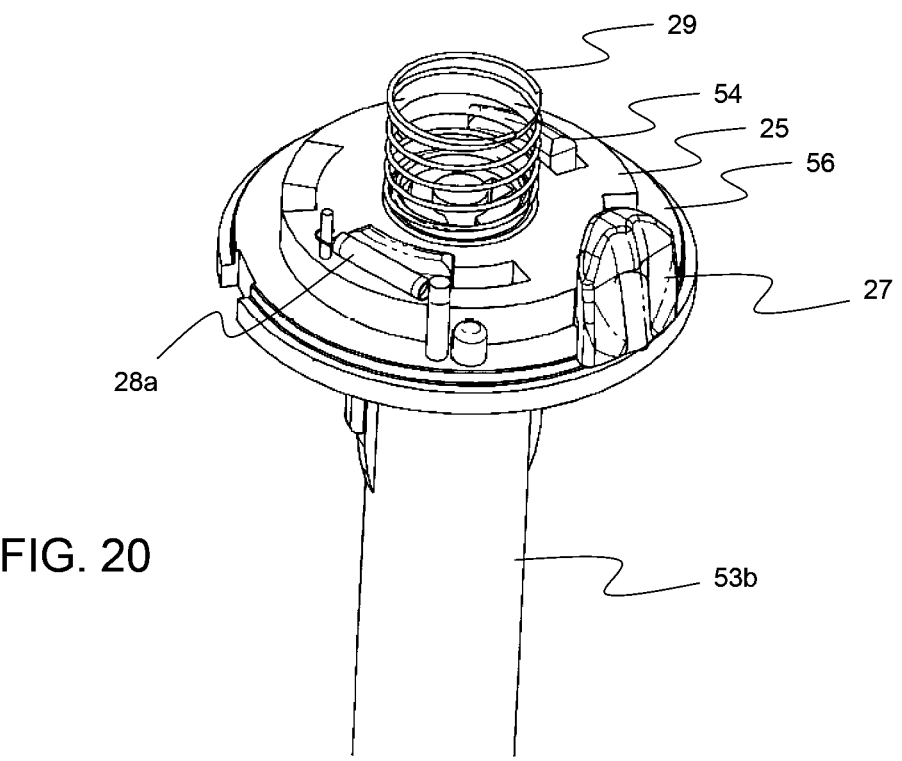
FIGS. 20-23 are perspective views of a shielded bladed obturator with various components removed/hidden in accordance with various aspects of the present invention.
Figure 21:
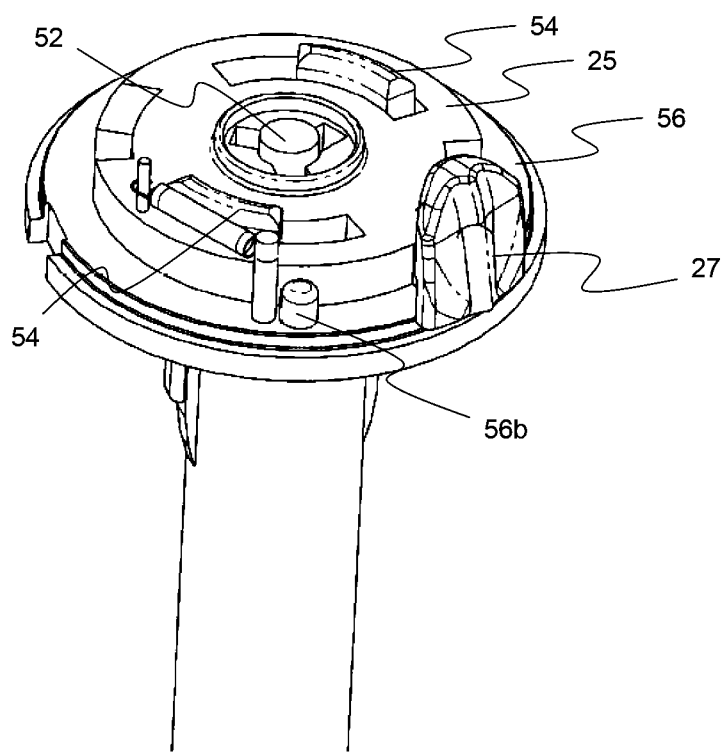
Figure 22:
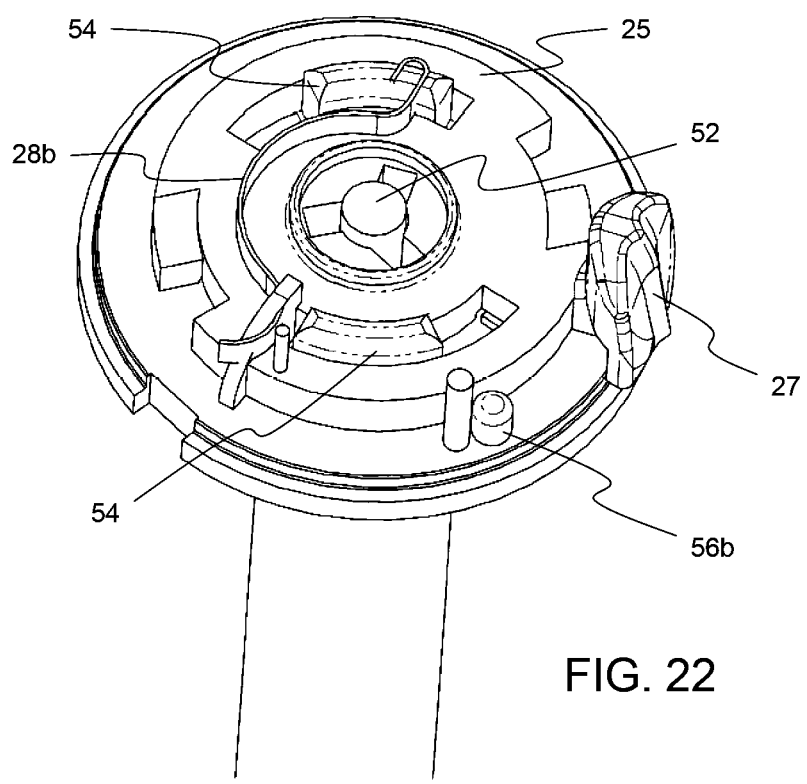
Figure 23:
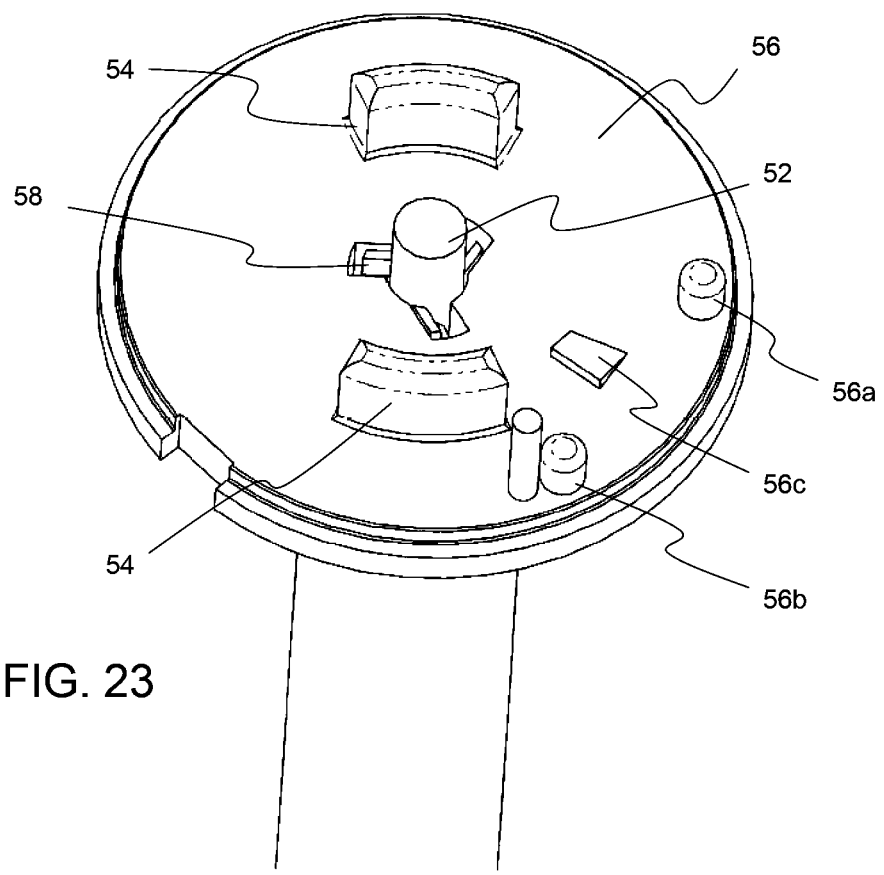

Pressure or force on the cam shaft 92 causes the cam shaft 92 to retract and exposes the blade 35 for cutting. In FIGS. 16-18, as the cam shaft 92 retracts, the flange 92a of the cam shaft 92 travels along the cam surface 98a and thereby forces the switch 91 to rotate towards the locked position, e.g., clockwise. As the switch 91 rotates, the extension spring 97 connected to the switch 91 also rotates towards the locked position. In one aspect, the switch 91 rotates about 180 degrees from the unlocked position back to the locked position. When the switch 91 has rotated about 120 degrees or such that the extension spring 97 is on an opposing side of the centroid relative to the unlocked position of the switch 91, the extension spring 97 generates a moment that forces the switch to rotate towards the locked position, e.g., clockwise. The flange 92a of the cam shaft 92 engaged with an opposing surface 98b of the switch 91 limits completion of the rotation of the switch 91 to the locked position. As the cam shaft 92 moves forward due to removal of pressure or force on the cam shaft 92 and through assistance of the compression spring, the flange 92a clears the surface 98b of the switch 91. The switch 91 unobstructed completes the rotation towards the locked position. The flange 91a again obstructs the flange 92a of cam shaft 92 preventing retraction of the cam shaft 92 and thus exposure of the blade 35 for cutting.

In one aspect, an arming or lockout mechanism is provided to prevent inadvertent exposure of the blades. In one particular aspect, a lever is coupled to the handle of the obturator. The lever is manually actuated to unlock the shield that protects the cutting blade. In about the center of the lever is a keyway which when rotated, aligns with the keys on the generally center shield shaft of the obturator. In operation, the obturator is pushed into the abdominal wall causing the shield to retract or pushed up. The opposite end that has the key, trips the lever, causing the lever to prepare to reset. Once through the abdominal wall, the shield moves forward protecting the blade and the lever resets itself to lock the shield.

Referring now to FIGS. 19-23, in one aspect, a handle 21 of a flat blade shielded obturator has a cover 23 and a switch 25 with a lever 27 extending from the switch. The switch 25 rests on base plate 56 from which outer shaft 53b extends. A compression spring 29 is placed between the cover 23 and the switch 25 biasing the switch 25 into position against the base plate 56. The connection between the switch 25 and cover 23 in one aspect is facilitated by tracks, detents or slots outlined on the switch 25 and/or cover 23. The spring 29 is coaxial with the longitudinal axis of the obturator and inner shaft 52. The inner shaft 52 is movable through an opening in the switch 25. The switch 25 also has one or more slots allowing and delimiting the rotation of the switch 25 and slidably connecting the slots 26 to projections 54 of base plate 56.

A return spring coupled to the switch 25 and base plate 56 biases the switch towards the initial or locked position. In one aspect, the return spring is an extension spring 28a that is connected to a post on the switch 25 and a post on the base plate 56. In one aspect, the return spring is a flat spring 28b that is connected to a flange on the switch 25 and to one of the projections 54 of base plate 56. A lever stop post 56a extending from the base plate 56 limits the rotation of the switch 25 as the switch is biased towards the locked position. Another lever stop post 56b extending from the base plate 56 delimits the unlocked position and limits the rotation of the switch 25 as the switch is moved towards the unlocked position. A lever lock ramp 56c extending from the base plate 56 engages a mating slot in the switch holding the switch in the unlocked position.

Figure 24:
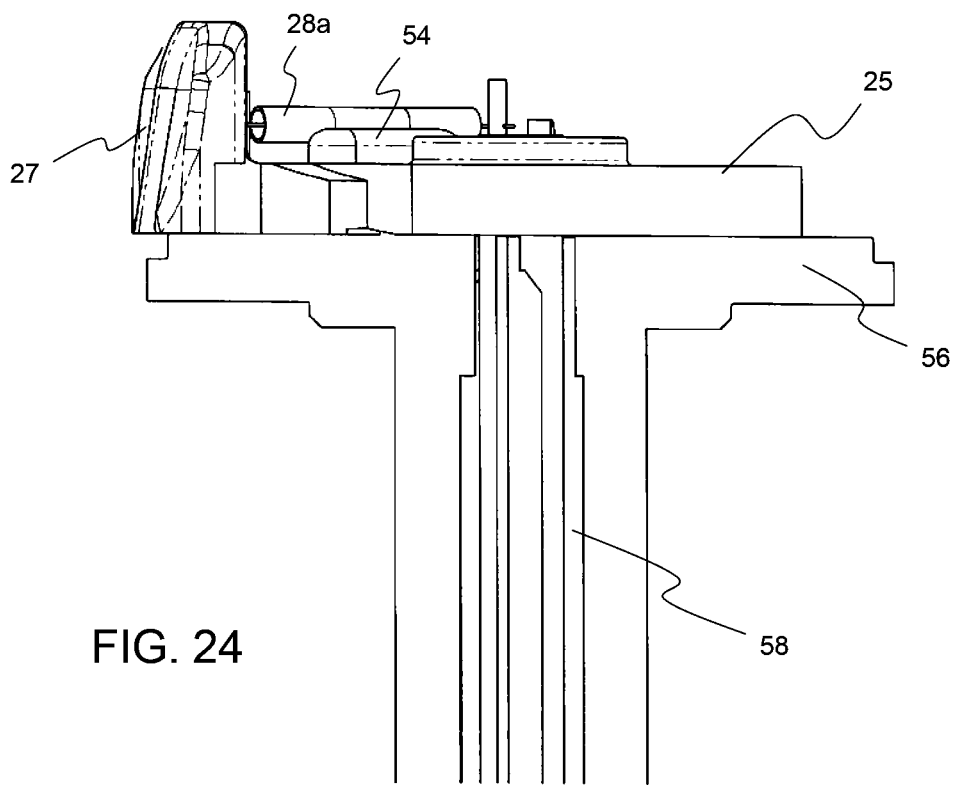
FIG. 24 is a cross-sectional side view of a shielded bladed obturator in accordance with various aspects of the present invention.
Figure 25:
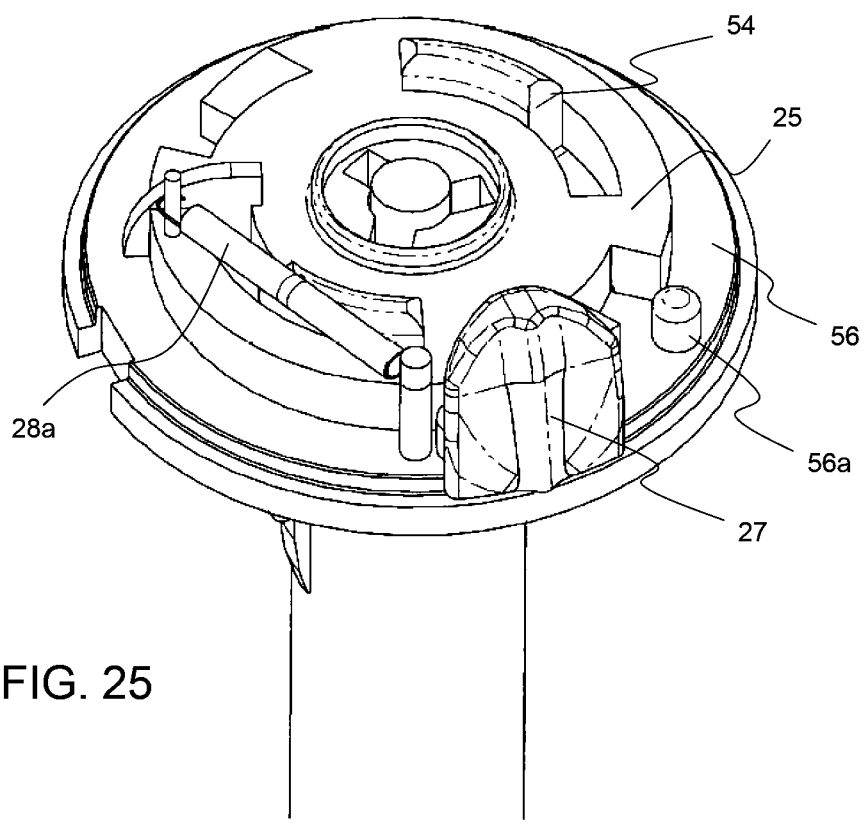
FIG. 25 is a perspective view of a shielded bladed obturator with various components removed/hidden in accordance with various aspects of the present invention.

Referring now also to FIG. 24, the inner shaft 52 has one or more keys 58 extending radially from the inner shaft. The one or more keys 58 are arranged to slide pass keyways in the base plate 56. Corresponding keyways 22 are situated in the switch 25. However, the keyways 22 are not aligned to the keys 58 of the inner shaft 52 when the switch 25 is in the locked position, thereby preventing longitudinal movement or retraction of the inner shaft 52 and thus the blade shield 33. In FIG. 25, the user through manipulation of the lever 27 extending from the switch 25 rotates the switch to the disarmed or unlocked position thereby aligning the keyways 22 on switch 25 to be aligned to the keys 58 on the inner shaft 52. Thus, the inner shaft 52 is unobstructed and thereby allowed to retract to expose the blade 35 for cutting.

Figure 26:
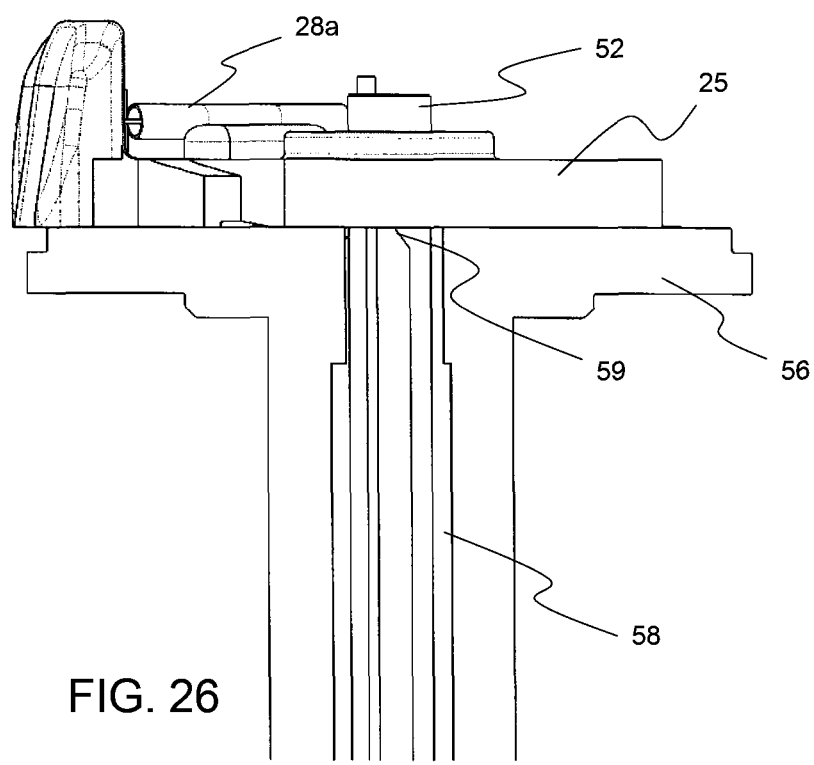
FIG. 26 is a cross-sectional side view of a shielded bladed obturator in accordance with various aspects of the present invention.
Figure 27:
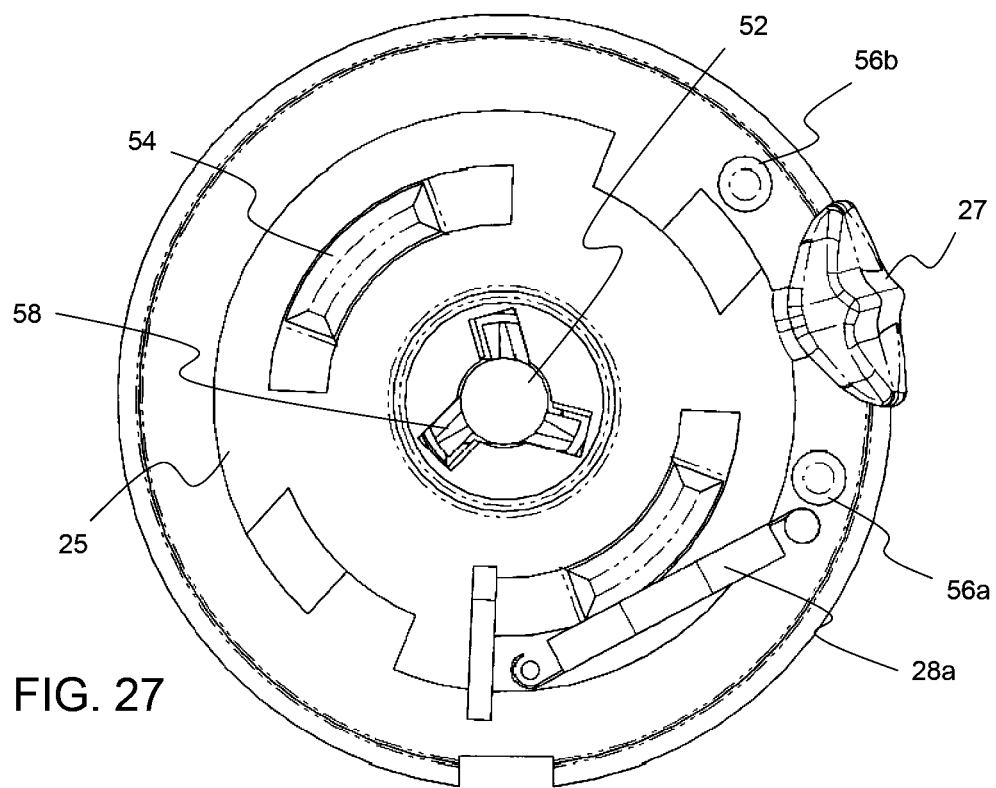
FIG. 27 is a top view of a shielded bladed obturator with various components removed/hidden in accordance with various aspects of the present invention.
Figure 28:
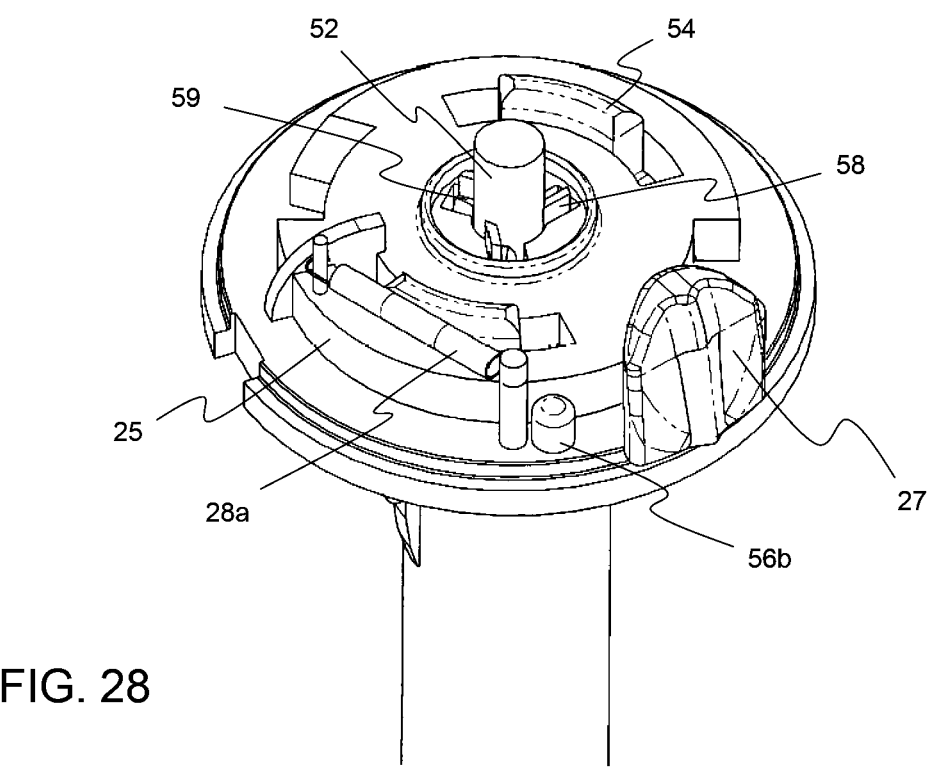
FIG. 28 is a perspective view of a shielded bladed obturator with various components removed/hidden in accordance with various aspects of the present invention.
Figure 29:
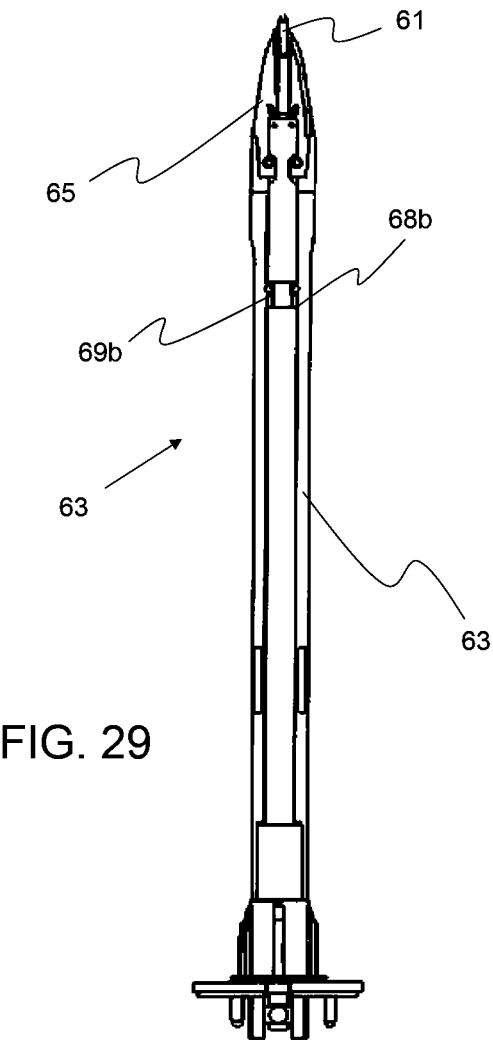
FIGS. 29-31 are side views of a shielded bladed obturator with various components removed/hidden in accordance with various aspects of the present invention.
Figure 30:
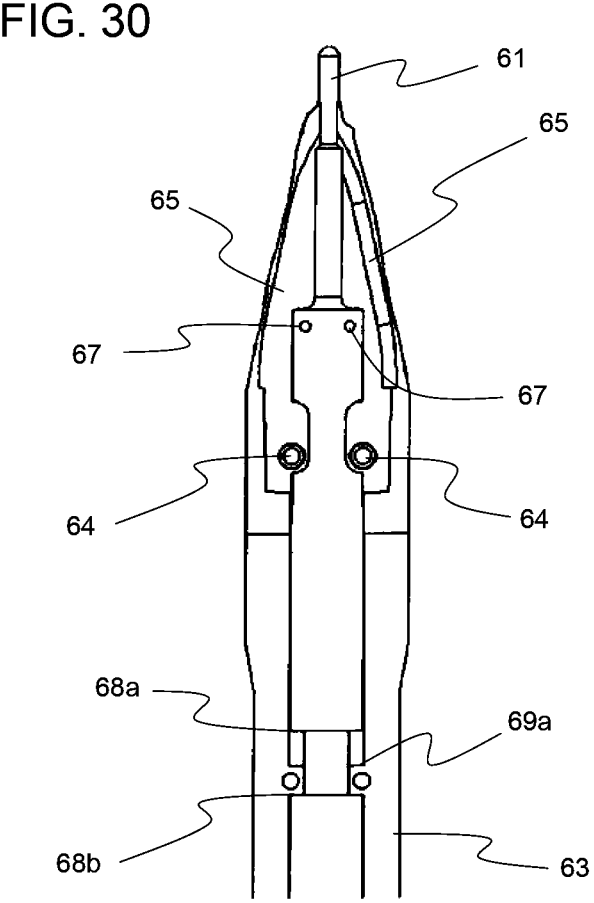
Figure 31:
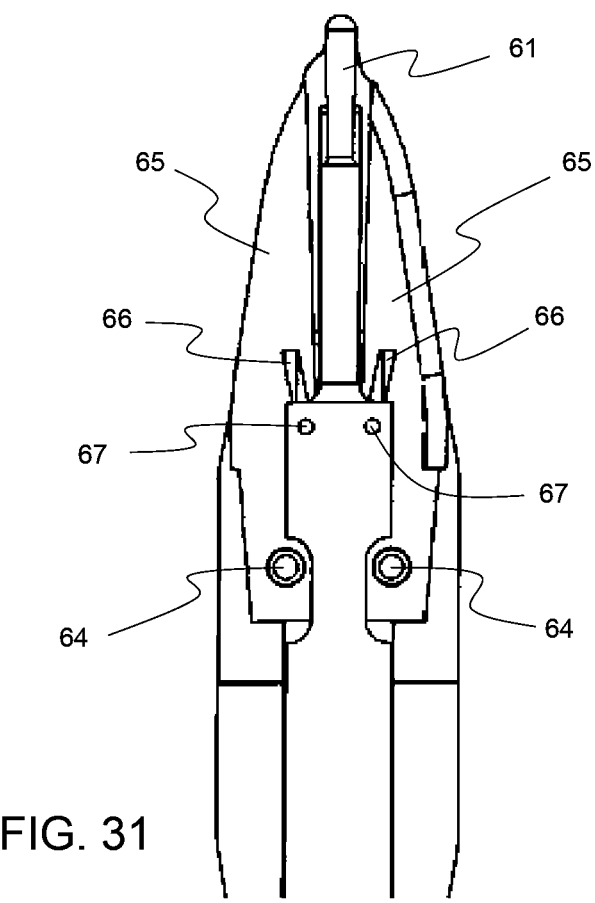
Figure 32:
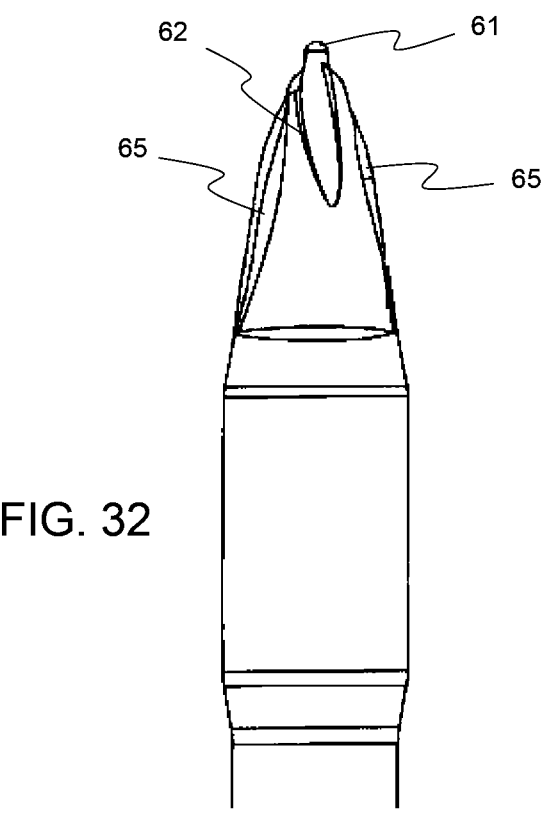
FIG. 32 is a side view of a shielded bladed obturator in accordance with various aspects of the present invention.
Figure 33:
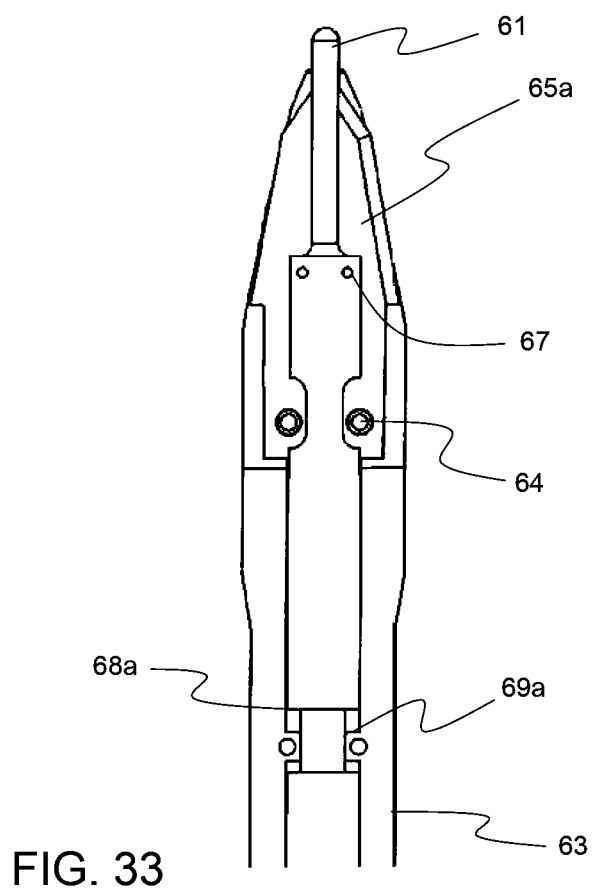
FIG. 33 is a side view of a shielded bladed obturator with various components removed/hidden in accordance with various aspects of the present invention.
Figure 34:
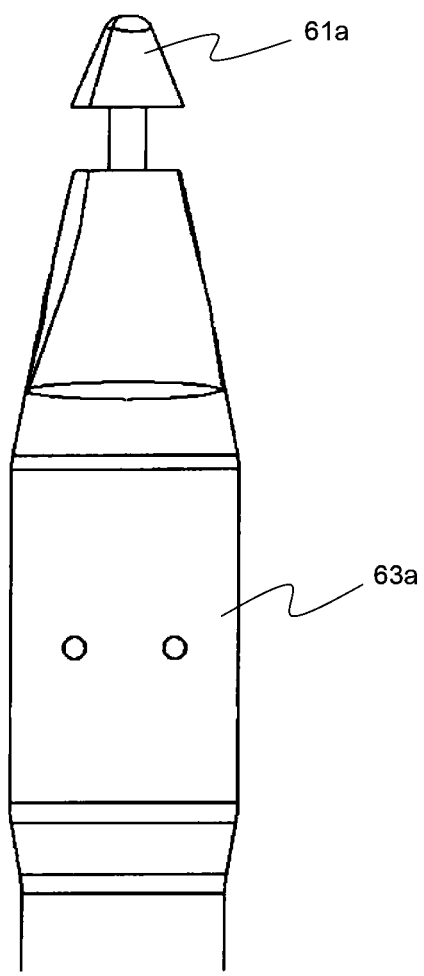
FIGS. 34-36 are side views of a shielded bladed obturator in accordance with various aspects of the present invention.
Figure 35:
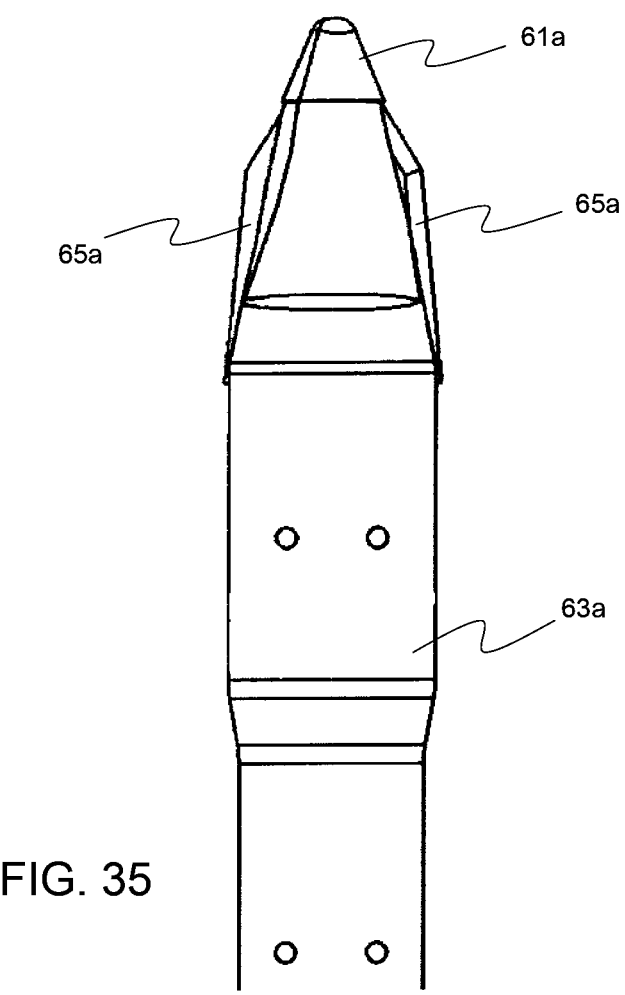
Figure 36:
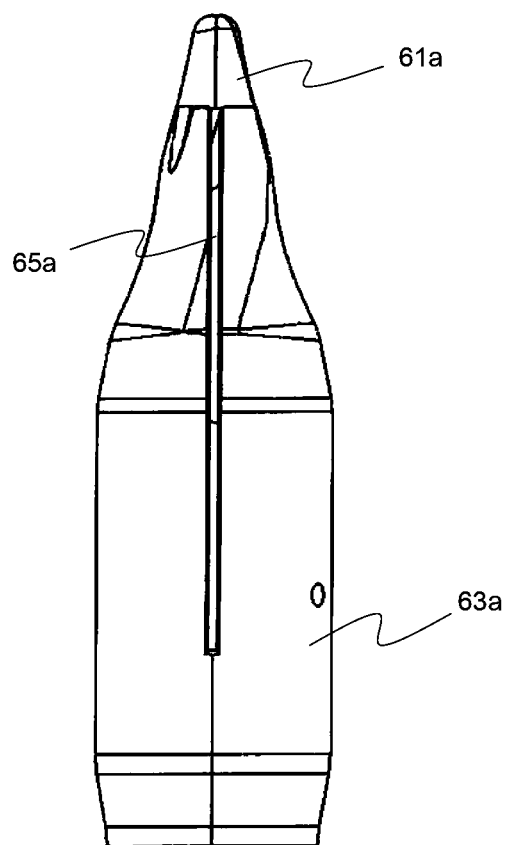
Figure 37:
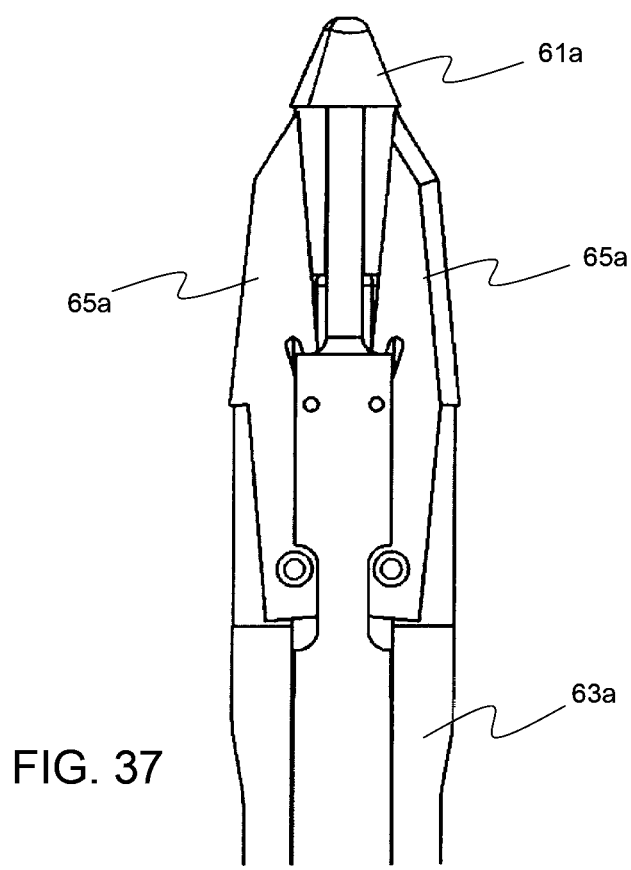
FIG. 37 is a side view of a shielded bladed obturator with various components removed/hidden in accordance with various aspects of the present invention.
Figure 38:
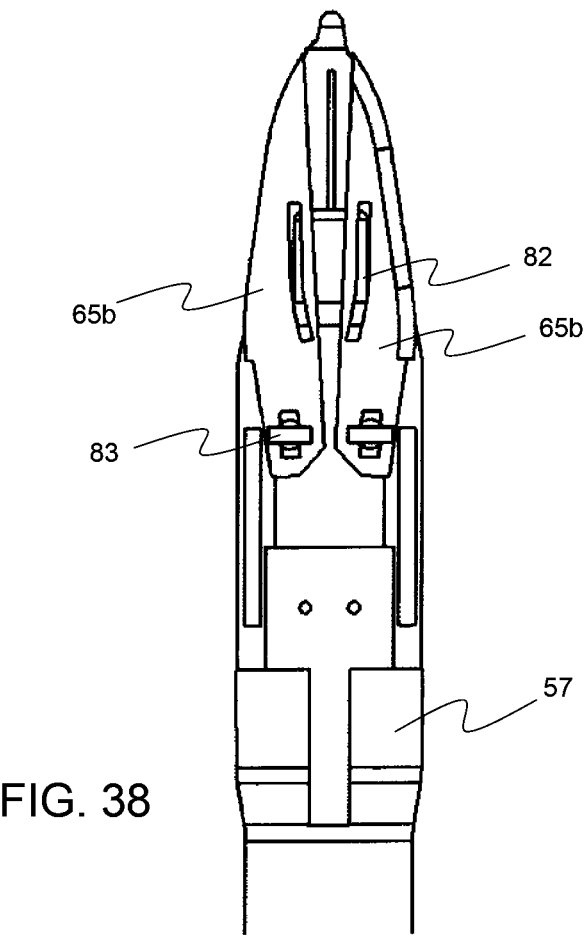
FIG. 38 is a side view of a shielded bladed obturator with various components removed/hidden in accordance with various aspects of the present invention.
Figure 39:
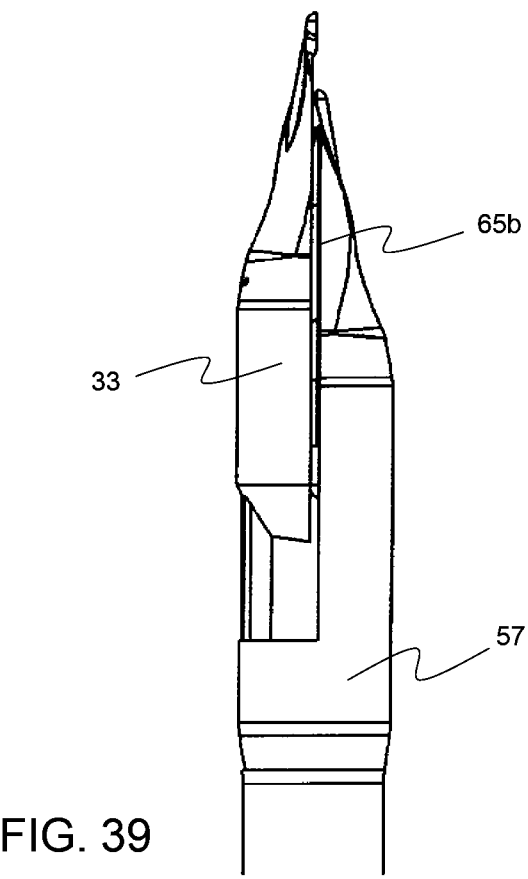
FIG. 39 is a side view of a shielded bladed obturator in accordance with various aspects of the present invention.
Figure 40:
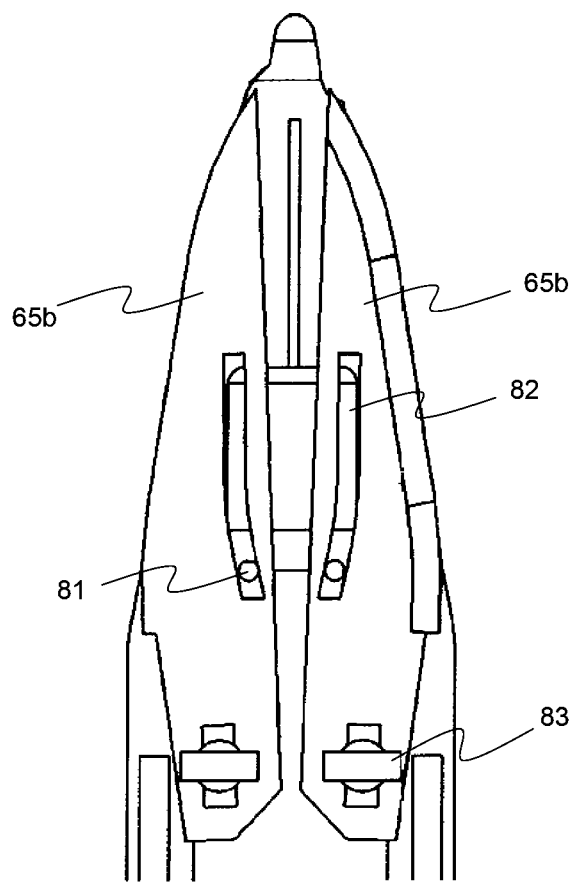
FIG. 40 is a side view of a shielded bladed obturator with various components removed/hidden in accordance with various aspects of the present invention.
Figure 41:
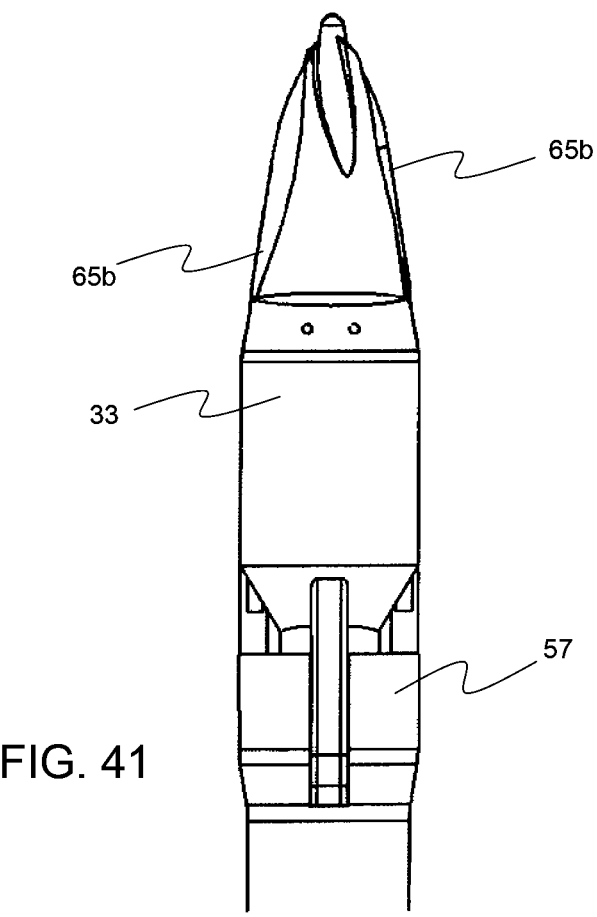
FIG. 41 is a side view of a shielded bladed obturator in accordance with various aspects of the present invention.

In FIGS. 26-28, as the blade shield retracts, the keys 58 travel through the keys 22 on switch 25. As the blade shield continues to retract, a cam surface 59 extending from one or more of the shield keys and/or the inner shaft 52 contacts and lifts the switch 25. The compressions spring 29 resists the lifting of the switch 25 thereby limiting travel of the switch. The lifted switch 25 is disengaged from the base plate 56 and thereby rotates back towards the locked position with the switch 25 being biased by the return spring. However, the keys 58 being situated in the keyways 22 limits complete rotation of the switch 25 towards the locked position. Thus, the blade shield is allowed to retract to expose the blade for cutting. Once the blade shield moves forward, i.e., external force or pressure is removed from the blade shield, the keys 58 also move out of the keyways 22 of the switch 25. With the keys 58 out of the keyways 22, rotational movement is unobstructed and thus under power of the return spring, the switch moves to the locked position. In the locked position, the switch 25 once again obstructs the path of the inner shaft 51 thereby locking or preventing movement of the blade shield 33 to expose the blade 35 for cutting.

In one aspect, through the center of the shield, a pin protrudes. The center pin is connected to individual blades by a cam assembly. The blades are locked to the shield by a pivot point. During use, as the tip of the obturator is pushed against the abdominal wall, the center pin is moved up into the shield. With the center pin connected to the blades by a cam assembly, the blades are extended out of the shield, to expose them. The blades remain exposed outside the shield as long as there is force on the center pin. When force is removed or reduced from the center pin, e.g., when the pin is through the abdominal wall, the center pin is allowed to reset to its initial position and cause the blades to retract. The obturator as such does not rely on friction to push or hold a shield back to expose the blades. Force at the tip of the obturator (e.g., on the center pin) displays the blades. Since the tip (center pin) can enter the abdominal cavity before the shield, the blades are exposed for less time inside the abdomen.

In FIGS. 29-32, an obturator 3 has a movable center pin 61. The center pin 61 slides forward and retracts back relative to a shaft 63 of the obturator 3. In one aspect, the center pin 61 extends from a movable shaft that is slides within a lumen of fixed inner shaft. The fixed inner shaft is encased or incorporated into an outer shaft. A flange or enlarged end 68a,b of the center pin 61 engaging with a flange or enlarged end 69a,b of the shaft 63 limits retraction of the pin 61. The pin 61 is largely encompassed or encased in the shaft 63. An aperture 62 in the tip of the shaft 63 allows passage of the pin 61. Also, a pair of opposing slots in the tip of shaft 63 allows passage of opposing pivoting blades 65. The blades 65 pivot on pivot pins 64 connected to the shaft 63.

One or more projections 67 extending from the center pin 61 interact with cam slots 66 in pivoting blades 65. Force or pressure on the center pin 61, retracts the center pin thereby engaging the cam slots 66 of the blades 65 to cause the blades to pivot and be exposed, e.g., displayed outside the shaft via slots in the shaft 63. As force/pressure is removed from the center pin 61, a spring coupled to the pin biases the pin forward causing the blades to retract. Referring to FIGS. 33-37, in one aspect, the slots 66 in the blades 65a may be further angled or curved to vary, regulate or control the speed and/or time of the blades' exposure. For example, the blades 65 or cam slots 66 in the blades 65 may be angled to expose a portion of the blade, e.g., the tips or distal portions, while covering the remaining portion of the blade to enhance cutting of the tissue or increasing covering of the blade after use. In one aspect, the size and/or shape of the center pin 61a is enlarged or curved to regulate or control the speed and/or time of the blades' exposure. In one aspect, the tip or end of the obturator acts as the center pin 61a. An enlarged end increases the contact surface area of the center pin 61a providing quicker and/or less precise activation to deploy the blades 65a. Channels within the center pin 61a and the shaft 63a allow the range of movement of the pivoting blades 65a.

In FIGS. 38-41, a movable portion of the shaft, e.g., the blade shield 33, has one or more projections 81 interacting with cam slots 82 in pivoting blades 65b. The blades 65b pivot on pivot pins 83 connected to the fixed shaft. In one aspect, the pivot pins and corresponding slots in the blades 65b have barbs or teeth further securing the blades to the blade shield 33. Force or pressure on the blade shield 33 retracts the blade shield thereby engaging the cam slots of the blades to cause the blades to pivot and be exposed, e.g., displayed outside the shaft. As force/pressure is removed from the movable shaft portion, the compression spring coupled to the blade shield 33 biases the blade shield 33 forward causing the blades to retract or pivot closed.

Figure 42:
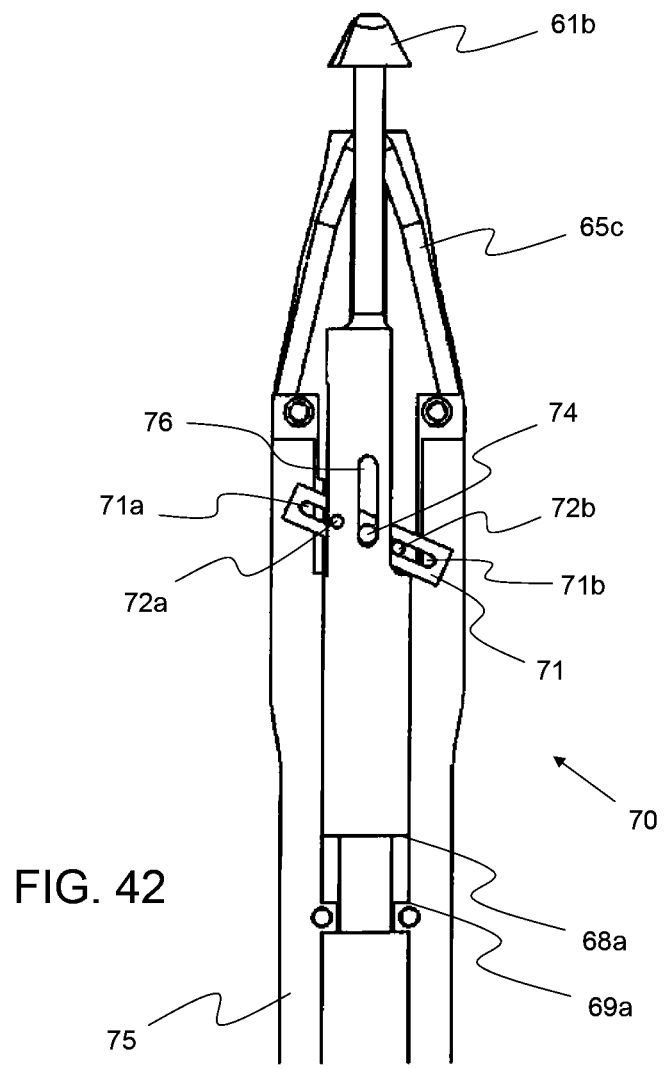
FIGS. 42-43 are side views of a shielded bladed obturator with various components removed/hidden in accordance with various aspects of the present invention.
Figure 43:
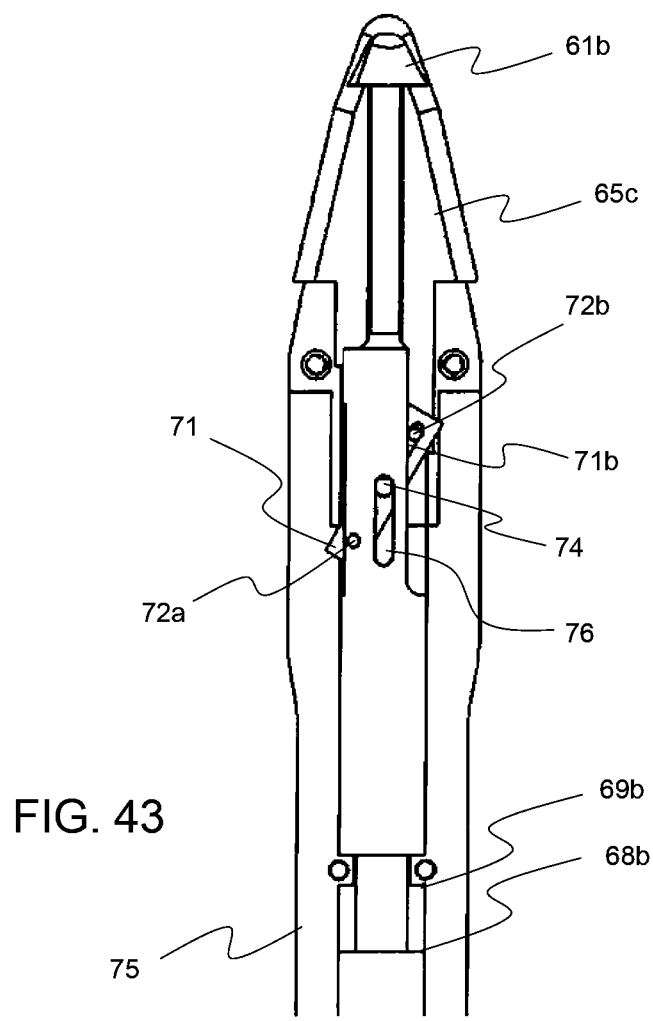
Figure 44:
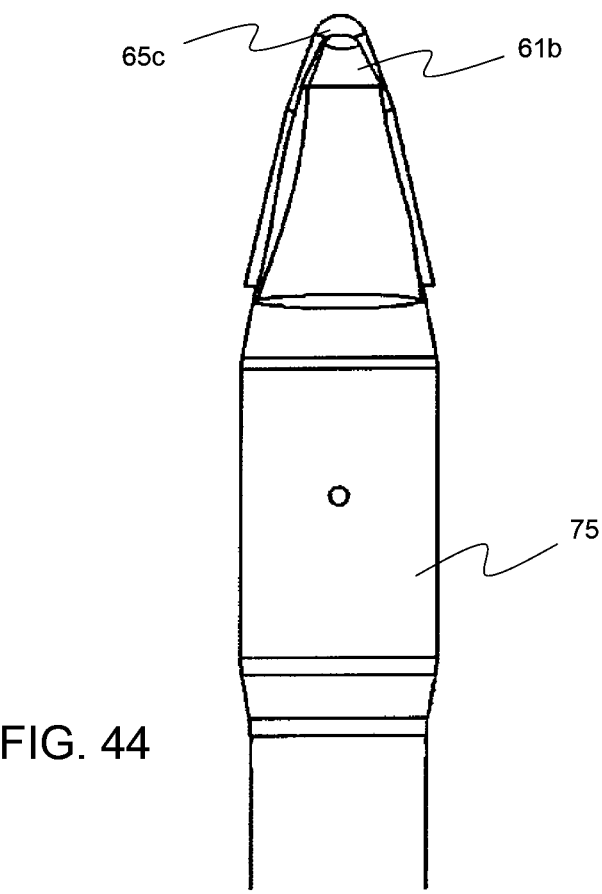
FIG. 44 is a side view of a shielded bladed obturator in accordance with various aspects of the present invention.

In one aspect, as shown in FIGS. 42-44, the center pin 61b and single blade 65c are connected by a linkage 70. When the center pin 61b is pushed on, it is forced into the shaft 75. While it is being pushed in, the linkage 70 transmits the motion and pushes the blade 65c forward, exposing it. The linkage, in one aspect, is rotationally attached to a shaft 75 of the obturator via a pin or post 74. The post 74 extends through a slot 76 in the center pin 61b. A pivot plate 71 is also connected to the post 74 with the post 74 acting as a pivot point for the plate 71. Channels within the center pin 61b and the shaft 75 allow the range of movement of the pivot plate 71.

Pin 72a is connected to the center pin 61b and extends through a cam slot 71a on plate 71. Pin 72b is connected to the blade 65c and extends through a cam slot 71b on plate 71. As such, as the center pin 61b retracts, the pin 72a retracts following the movement of the center pin 61b. The pin 72a engages the cam slot 71a of the plate 71 causing the plate 71 to rotate about the post 74. The cam slot 71b engages the pin 72b causing the blade 72b to advance or move in the opposite direction of the center pin 61b thereby exposing the blade 65c for cutting. As pressure or force is lost on the center pin 61b, the center pin moves back to its original position. Movement of the center pin back reverses the linkage, i.e., causing the plate 71 to rotate in the opposite direction. Thus, the blade 65c retracts into the shaft 75.

The retractable blade mechanisms described above may be used in conjunction with the previously described arming or locking shield mechanisms. For example, a switch in the locked position can prevent retraction of a center pin thereby preventing the extension or pivoting of the blade or blades.

Accordingly, the present invention provides a bladed shielded obturator. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. An obturator comprising:
   a handle, the handle having a rotatable switch arranged to rotate about a rotational axis from a first position to a second position and a biasing spring positioned within the handle and coupled to the rotatable switch; and
   a shaft connected to the handle and having a longitudinal axis parallel with the rotational axis, the shaft having a movable portion, a fixed portion with a blade connected to the fixed portion of the shaft, and a compression spring surrounding a portion of the movable portion and biasing the movable portion longitudinally distally relative to the fixed portion;
   the rotatable switch in the first position obstructing the movable portion of the shaft to prevent entry of the movable portion of the shaft into the handle and movement of the movable portion of the shaft along the longitudinal axis and in the second position freeing the movable portion of the shaft to allow entry of the movable portion of the shaft into the handle and movement of the movable portion of the shaft along the longitudinal axis.

2. The obturator of claim 1 wherein the switch in the first position is biased by the biasing spring towards the first position and the switch in the second position is biased by the biasing spring towards the second position.

3. The obturator of claim 1 wherein the switch has a slot, the slot being aligned with the shaft when the switch is in the second position.

4. The obturator of claim 3 wherein the slot has a cam surface engagable with the shaft converting translational motion of the shaft to rotational motion of the switch.

5. The obturator of claim 1 wherein the movable portion extends beyond the blade and the blade extends beyond the fixed portion with portions of the blade being exposed.

6. The obturator of claim 5 wherein the movable portion slides within the fixed portion.

7. The obturator of claim 4 wherein an inner shaft connects the movable portion of the shaft to the switch, the inner shaft having a flange engageable with the cam surface of the switch.

8. The obturator of claim 1 wherein the blade comprises a plurality of pivotable blades.

9. The obturator of claim 8, wherein each blade is pivotable to extend outside the fixed portion of the shaft and retract inside the fixed portion of the shaft.

10. The obturator of claim 8 wherein each blade of the plurality of pivotable blades has a cam slot engagable with a pin extending from the movable portion of the shaft.

11. The obturator of claim 1 wherein the fixed portion of the shaft encompasses the movable portion of the shaft.

12. The obturator of claim 1 wherein the blade is retractable into the fixed portion of the shaft and extendable out of the fixed portion of the shaft.

13. The obturator of claim 1 wherein the movable portion of the shaft has a key surface extending radially from the movable portion of the shaft.

14. The obturator of claim 13 wherein the switch has radially extending keyway slot.

15. The obturator of claim 14 wherein the switch in the first position misaligns the keyway slot with the key surface of the movable portion of the shaft and the switch in the second position aligns the keyway slot with the key surface of the movable portion of the shaft.

16. The obturator of claim 15 wherein the key surface of the movable portion of the shaft has a cam surface engageable with the switch causing rotational movement of the switch.

17. An obturator comprising:
a handle having a cover with an opening and a manually engagable switch arranged to rotate about a rotational axis from a first position to a second position, the switch having a lever protruding through the opening in the first position, the lever manually pivotable with respect to the cover to rotate the switch to the second position, and the switch recessed within the cover in the second position; and
a shaft connected to the handle and having a longitudinal axis parallel with the rotational axis, the shaft having a movable portion and a fixed portion with a blade connected to the fixed portion of the shaft;
the switch preventing movement of the movable portion of the shaft along the longitudinal axis in the first position and allowing movement of the movable portion of the shaft in the second position.

18. The obturator of claim 17 further comprising means for rotationally biasing the switch.

* * * * *